(12) United States Patent
Gontarz

(10) Patent No.: US 10,517,808 B2
(45) Date of Patent: Dec. 31, 2019

(54) ORAL CARE FORMULATION AND METHOD FOR THE REMOVAL OF TARTAR AND PLAQUE FROM TEETH

(71) Applicant: John A. Gontarz, Landenberg, PA (US)

(72) Inventor: John A. Gontarz, Landenberg, PA (US)

(73) Assignee: TARTAREND, LLC, Landenberg, PA (US)

( * ) Notice: Subject to any disclaimer, the term of this patent is extended or adjusted under 35 U.S.C. 154(b) by 0 days.

(21) Appl. No.: 15/538,121

(22) PCT Filed: Dec. 15, 2016

(86) PCT No.: PCT/US2016/066875
§ 371 (c)(1),
(2) Date: Jun. 20, 2017

(87) PCT Pub. No.: WO2017/106467
PCT Pub. Date: Jun. 22, 2017

(65) Prior Publication Data
US 2018/0271765 A1    Sep. 27, 2018

Related U.S. Application Data

(60) Provisional application No. 62/267,354, filed on Dec. 15, 2015, provisional application No. 62/287,538, filed on Jan. 27, 2016.

(51) Int. Cl.
*A61K 8/49*    (2006.01)
*A61Q 11/00*   (2006.01)
*A61K 8/20*    (2006.01)

(52) U.S. Cl.
CPC ............. *A61K 8/4973* (2013.01); *A61K 8/20* (2013.01); *A61Q 11/00* (2013.01); *A61K 2800/30* (2013.01); *A61K 2800/92* (2013.01)

(58) Field of Classification Search
None
See application file for complete search history.

(56) References Cited

U.S. PATENT DOCUMENTS 3,271,242 A    9/1966  McNicholas et al.
3,591,515 A    7/1971  Lovely
(Continued)

FOREIGN PATENT DOCUMENTS

EP    0 613 678 A1    9/1994
WO    2013089716 A1   6/2013

OTHER PUBLICATIONS

SM Berge, LD Bighley, DC Monkhouse. "Pharmaceutical Salts." Journal of Pharmaceutical Sciences, vol. 66 No. 1, Jan. 1977, pp. 1-19. (Year: 1977).*

(Continued)

*Primary Examiner* — Isaac Shomer
(74) *Attorney, Agent, or Firm* — Volpe and Koenig, P.C.

(57) ABSTRACT

An oral care formulation and method for removing tartar and plaque from the teeth, gums, and oral cavity is disclosed. The oral care formulation can take the form of a toothpaste, gel, wash, rinse, soak, spray, chewing gum, dental floss, or other suitable delivery system, containing a therapeutically effective amount of dimethyl isosorbide (DMI) (or equivalent or analog thereof) and chlorine dioxide ($ClO_2$) for removal of tartar and plaque.

21 Claims, 15 Drawing Sheets

(56) References Cited

U.S. PATENT DOCUMENTS

| | | | |
|---|---|---|---|
| 3,887,712 | A | 6/1975 | Lover et al. |
| 3,988,433 | A | 10/1976 | Benedict |
| 4,060,600 | A | 11/1977 | Vit |
| 4,083,955 | A | 4/1978 | Grabenstetter et al. |
| 4,119,711 | A | 10/1978 | Hernestam et al. |
| 4,160,821 | A | 7/1979 | Sipos |
| 4,178,363 | A | 12/1979 | Miller, Jr. |
| 4,585,649 | A | 4/1986 | Lynch |
| 4,610,871 | A | 9/1986 | Lynch |
| 4,627,974 | A | 9/1986 | Lynch |
| 4,627,979 | A * | 12/1986 | Lynch ............... A61Q 11/00 424/48 |
| 4,925,656 | A * | 5/1990 | Ratcliff ............... A01N 59/00 424/53 |
| 5,198,220 | A | 3/1993 | Damani |
| 5,242,910 | A | 9/1993 | Damanj |
| 5,603,921 | A | 2/1997 | Bowen |
| 6,039,934 | A * | 3/2000 | Alliger ............... A61K 33/20 424/53 |
| 8,303,938 | B2 | 11/2012 | Andersen |
| 2003/0095929 | A1 | 5/2003 | Stier |
| 2008/0025926 | A1 * | 1/2008 | Kavouklis ............... A61K 8/22 424/53 |
| 2010/0221198 | A1 | 9/2010 | Ratcliff |
| 2014/0341818 | A1 * | 11/2014 | Hourigan ............... A61K 8/347 424/49 |
| 2015/0030546 | A1 | 1/2015 | O'Malley |

OTHER PUBLICATIONS

Mitchell, J. Can You Remove Tartar At Home? https://www.colgate.com/en-us/oral-health/basics/threats-to-dental-health/can-you-remove-tartar-at-home-.

Lewis, C. Fighting Gum Disease: How to Keep Your Teeth. https://www.colgate.com/en-us/oral-health/conditions/gum-disease/fighting-gum-disease-how-to-keep-your-teeth.

How to Get Rid of Plaque and Remove Tartar Buildup. https://oralb.com/en-us/oral-health/conditions/tartar-plaque/how-to-get-rid-of-plaque-remove-tartar-buildup.

International Search Report mailed in corresponding International Patent Application No. PCT/US2016/066975 dated Feb. 23, 2017, consisting of 5 pp.

Written Opinion mailed in corresponding International Patent Application No. PCT/US2016/066975 dated Feb. 23, 2017, consisting of 11 pp.

* cited by examiner

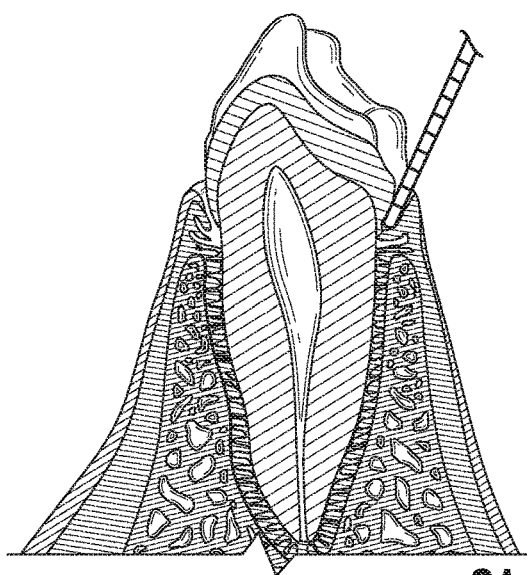 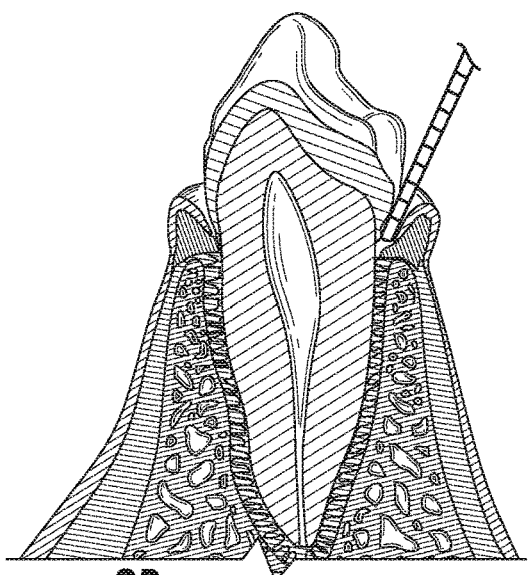
FIG. 2A   FIG. 2B
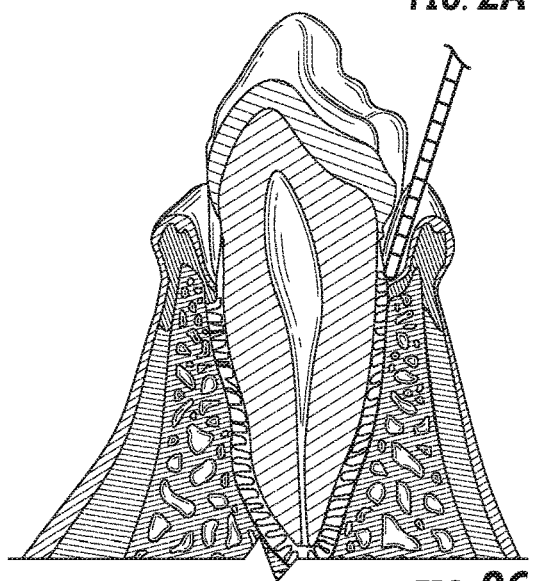 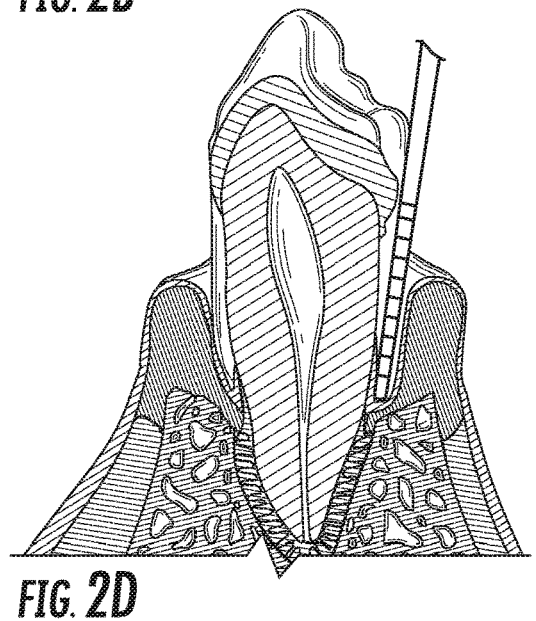
FIG. 2C   FIG. 2D
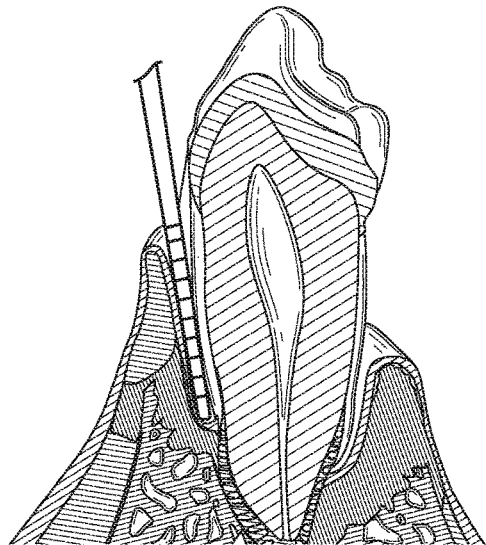
FIG. 2E

ORAL CARE FORMULATION AND METHOD FOR THE REMOVAL OF TARTAR AND PLAQUE FROM TEETH

CROSS REFERENCE TO RELATED APPLICATIONS

This application is a 35 U.S.C. § 371 national stage application of International Application No. PCT/US16/66875, which was filed on Dec. 15, 2016, and claims the benefit of U.S. Provisional Patent Application No. 62/287,538, filed Jan. 27, 2016, and U.S. Provisional Patent Application No. 62/267,354, filed Dec. 15, 2015, all of which are incorporated herein by reference as if fully set forth.

FIELD

An oral care formulation and method for removing tartar and plaque from the teeth, gums, and oral cavity is provided. The oral care formulation can take the form of a toothpaste, gel, wash, rinse, soak, spray, chewing gum, dental floss, or other suitable delivery system, containing a therapeutically effective amount of dimethyl isosorbide (DMI) (or equivalent or analog thereof) and chlorine dioxide ($ClO_2$) for removal of tartar and plaque.

BACKGROUND

Over the years, numerous consumer products have been manufactured and marketed for cleansing teeth of tartar and plaque. The products have taken the form of toothpastes, powders, gels, liquid rinses, chewing gum, dental floss, or other suitable delivery systems. The formation of tartar and plaque on clean teeth is a complex process, which begins with bacteria in the mouth.

This process begins within a few minutes after the teeth have been professionally cleaned by a dentist or hygienist. The first bacteria start attaching to the pellicle on the tooth surface, tongue, and gums. This first layer of bacteria allows other bacteria to attach. These bacteria then multiply by cell division to form a complex structure called a biofilm. After two to three hours, the biofilm thickness increases to the point that a visible film of bacteria can be seen by the naked eye.

This visible film of bacteria is called plaque and, over time, the bacteria in protected areas of the mouth grow into thick structures known as mature plaque. If this plaque is not disturbed by flossing or brushing, it begins to mineralize as calcium and phosphate ions from saliva start to deposit within the bacterial colony and harden to form crystalline tartar. Most toothpaste achieves their cleaning action from abrasives which can comprise about 50% of the typical toothpaste. These insoluble abrasives help remove plaque from accessible portions of the teeth. Brushing, however, will not remove tartar. Traditional toothpaste and other traditional mouth rinses can help prevent tartar buildup, but they cannot remove it once it has formed. Until now, only a dental hygienist or dentist could remove tartar by physically scraping it from the tooth surface with specialized metal instruments. The physical process by which a dentist or hygienist scrapes tartar from teeth is called "scaling." During a scaling, the dentist or hygienist uses special stainless steel instruments to remove tartar from the teeth both above and below the gum line.

Dental plaque is a biofilm (usually a pale yellow to whitish color) that builds up on the surface of teeth. If not removed regularly, it can lead to dental cavities (caries) or periodontal problems (such as gingivitis). The microorganisms that form the biofilm are almost entirely bacteria (mainly *Streptococcus* and anaerobes), with the composition varying by location in the mouth. The microorganisms present in dental plaque are all naturally present in the oral cavity, and are normally harmless. However, failure to remove plaque allows it to build up in a thick layer and leads to increased bacterial growth.

Dental plaque is a precursor of tartar, which is also known as calculus. Both terms, "tartar" and "calculus," are used interchangeably to refer to mineralized dental plaque, where the mineral may be calcium. This build-up of hardened (mineralized) plaque on the teeth is formed by the presence of saliva, debris, glucans, and minerals. Typically tartar is primarily comprised of four or more calcium phosphate mineral salts, including octacalcium phosphate, hydroxyapatite, whitlockite, and brushite. These salts are deposited within and between remnants of the biofilm and plaque bacterial colony. Mature tartar consists of an inorganic portion which is largely calcium phosphate arranged in a hydroxyapatite crystal lattice structure similar to bone, enamel, and dentine. An organic portion is also present and consists of desquamated epithelial cells, leukocytes, glucans, salivary sediment, food debris, and various types of microorganisms. The rough surface of mature tartar provides an ideal medium for bacterial growth, threatening the health of the gums and absorbing unaesthetic stains far more easily than natural teeth.

The longer that tartar, plaque, and the bacteria they protect remain on the teeth, the more damage they can cause. Initially, accumulation of tartar, plaque, and bacteria may simply irritate and inflame the gingiva, the part of the gum around the base of the teeth. This is called gingivitis, the mildest form of periodontal disease. Ongoing inflammation eventually causes pockets to develop between the gums and teeth that fill with plaque, tartar and bacteria. Bacteria can deposit endotoxins—a byproduct of their own metabolism—which are responsible for much of the inflammation that can be caused around teeth. In time, these pockets in the gums become deeper and, as more bacteria accumulate, eventually advance under the gum tissue. These deep infections can cause a loss of tissue and bone. If too much bone or tissue is destroyed, one or more teeth may be lost.

There are two basic forms of tartar. Supragingival (outside the gums) tartar is the visible deposit that forms on the top of the teeth. Subgingival (inside the gums) tartar forms in pockets between teeth and gums. Subgingival tartar is more harmful because it promotes faster growth of bacteria. Buildup of tartar often causes swelling, bleeding and weakening of gums, and can lead to gum recession and tooth loss. Tartar can even extend into pockets created between the teeth and gums. The anaerobic bacteria found in pockets around teeth may be linked to cardiovascular disease and pre-term low birth weight babies. These pockets are difficult to reach by tooth brushing, and are not affected by standard mouthwashes.

Regularly scheduled teeth cleanings every six months with a dentist or dental hygienist where scaling of the teeth is performed can be effective for the removal of accumulated tartar and plaque. Scheduling regular professional dental cleanings, however, can be difficult in areas where access to a dental professional is limited or the demands of busy schedules require the cancellation or postponement of professional teeth cleanings. Moreover, certain individuals can be genetically predisposed to the rapid formation and accumulation of tartar, which requires more frequent (usually every three months) professional dental cleanings than the typical six-month interval.

Although the mechanical dental scaling procedure may be effective in tartar removal, in addition to being very time-consuming, this procedure has several disadvantages. One disadvantage of dental scaling is that the process can destroy dental cementum, which is a tooth formation critical to gum/tooth attachment. Another disadvantage of dental scaling is that the treatment may remove healthy gum tissue, which cannot regenerate. Still another disadvantage is that the procedure is painful and often causes bleeding and swelling of the gums when tartar accumulation is substantial. An economic disadvantage is that dental scaling is almost exclusively done by a dental professional and is relatively expensive.

A variety of chemical and biological agents have been suggested to retard tartar formation. Pyrophosphate salts and other chemical agents are known to have the ability to retard tartar formation. Current anti-tartar oral formulations designed for preventing the accumulation of tartar on the teeth often incorporate as an active ingredient sodium pyrophosphate, tetrasodium pyrophosphate, or other types of pyrophosphate compounds to prevent calcium phosphate salts from depositing on the enamel of teeth. One example can be found in U.S. Pat. No. 8,303,938. Compounds containing pyrophosphate, however, can result in tooth sensitivity and mouth lesions in some individuals. Moreover, none of the anti-tartar oral formulations containing pyrophosphate compounds are very effective at actively removing tartar from teeth once the calcium phosphate salts have bonded with tooth enamel.

Other chemicals reportedly have been used to inhibit the formation of plaque and calculus on teeth. For example, in U.S. Pat. No. 4,610,871 describes the use of monoalkyl or dialkyl ethers of dianhydrohexitols to inhibit the formation of plaque and calculus on teeth is described. U.S. Pat. No. 4,178,363 describes the use of n-undecylenic acid or a calcium or zinc salt thereof for reducing dental plaque and infections of the teeth and gums. U.S. Pat. No. 4,119,711 describes spiro 1-(hydroxyalkyl) piperidino derivatives, which have efficacy in reducing the formation of plaque. Additionally, U.S. Pat. No. 3,887,712 discloses that alexidine dihydrofluoride is useful in the treatment of dental plaque, calculus, gingivitis, and related periodontal diseases. U.S. Pat. No. 4,160,821 discloses that a glycerin solution of zinc chloride or other acceptable zinc salts provides effective therapy for gingivitis when applied to the gingival and teeth. U.S. Pat. No. 4,060,600 teaches a method of treating teeth in dentistry, for the prevention of calculus, removal of caries, and dissolution of plaque, comprising applying an aqueous solution containing a hypochlorite of an alkali and/or alkaline earth metal, and an amino compound capable of forming water-soluble non-mucous irritating N-chloro and/or N-dichloro derivatives thereof to the teeth. All of these chemical and biological agents have some disadvantages, such as limited effectiveness, discoloration of teeth or tongue, desquamation and soreness of oral mucosa, objectionable taste, toxicity, and may also cause an imbalance of the oral flora.

Dimethyl isosorbide (DMI) is a hydrophilic and highly polar compound. DMI is a non-toxic solvent and carrier that is considered to be neither a primary irritant to human skin nor a skin sensitizer. DMI also provides a safe and effective delivery enhancement mechanism for active ingredients in skin care products, such as sunless tanners, facial and eye-zone treatments, skin serums, anti-acne formulations and make-up removers.

DMI was studied in the 1980's for use in dentifrices and oral care formulations for inhibiting the formation of plaque and calculus in the mouth (Lynch U.S. Pat. Nos. 4,585,649; 4,610,871; and 4,627,974). Lynch demonstrated that DMI has antibacterial properties against *Streptococcus mutans* and that DMI is a weak antibacterial at high concentrations. Lynch also observed that collected dental tartar was slowly dissolved by DMI in an occasionally stirred beaker over a 24 hour period at 100% and 50% aqueous concentrations. Lynch, however, did not provide any findings concerning whether DMI was capable of in vivo removal of tartar from teeth and gums.

DMI was considered for use as an antibacterial for oral applications in the 1980's and was heavily marketed into the personal care and oral health industries in the Americas, Europe, Australia, and Japan. DMI has been found to be an excellent delivery enhancer, which can place active ingredients where they are needed most on the skin. This functionality of DMI has been used in sunless tanners, facial and eye-zone treatments, skin serums, anti-acne formulations and make-up removers. In oral hygiene applications, DMI has found little if any use as a delivery enhancer in oral applications.

Originally, DMI was thought to have use as an antibacterial in oral applications, but its antibacterial functionality is weak and more effective anti-bacterials such as Triclosan (5-chloro-2-(2,4-dichlorophenoxy)phenol), chlorohexidine gluconate, and zinc and other metal salts are used as antibacterials in oral applications. As described above, DMI has shown some utility in dissolving tartar in vitro over a period of 24 hour, sustained exposure in the Lynch U.S. Pat. Nos. 4,627,974 and 4,610,871, but was not effective at removing tartar from subjects' teeth in vivo. DMI is also relatively expensive at nearly $100.00 per kilogram for personal care products. Where it is found in products, it is usually present in the 0.1% (w) to 2% (w) levels. Thus, DMI is only considered for high value delivery enhancement application in the personal care industry. Moreover, industry had largely abandoned research and the use of DMI in the oral hygiene setting as an unsuccessful, limited spectrum, oral antiseptic that was cost-prohibitive. There currently are no known commercial toothpastes or mouthwashes containing DMI for sale on the dental care market.

Chlorine dioxide ($ClO_2$) is a highly soluble gas that does not hydrolyze when combined with water. Instead, it remains dissolved as a gas in solution. Chlorine dioxide has been used as a powerful and safe disinfectant and biocide for almost 200 years, including for many industrial applications. More recently, chlorine dioxide has been used for removing bacteria and biofilm from cooling towers and potable water lines. When applied correctly, it has been shown to control a broad range of biofilms and bacteria.

Chlorine dioxide is strongly oxidizing and can be explosive in concentrations exceeding 10% (v/v). Because "active" chlorine dioxide, $ClO_2$, is highly reactive with other chemicals, it is often converted to a stabilized form for transporting and mixing, as described in McNicholas U.S. Pat. No. 3,271,242. Active chlorine dioxide can also be prepared at the time of use by combining chlorite source (for example sodium chlorite, potassium chlorite, or calcium chlorite) with a weak food or cosmetic grade acid (for example, citric acid, lactic acid, sodium bisulfate, or disodium phosphate), which produces chlorous acid as an intermediate, which in turn forms active chlorine dioxide. Stabilized chlorine dioxide and a two-part product, which uses sodium chlorite and weak organic acids such as citric acid have been available for many years, and have been largely used for industrial, bleaching, oxidizing and surface cleaning applications.

Chlorine dioxide has normally been used in industrial applications such as the whitening of paper pulp, and other bleaching and oxidizing activities. More recently chlorine dioxide has been found to be effective in disinfecting hard surfaces such as countertops and walls and is promoted to disinfect animal drinking water as well as other similar applications. Chlorine dioxide has a noticeable odor similar to chlorine, which is still noticeable at aqueous concentrations as low as 10 ppm. People working with high concentrations of chlorine dioxide must normally wear personal protective equipment to prevent possible skin and eye contact. Chlorine dioxide reacts with many organic compounds and under many conditions "active" chlorine dioxide has poor shelf stability. These facts either singularly or in combination normally dissuade most development personnel from considering chlorine dioxide as an additive to personal care products let alone oral care applications.

Recent advances have made chlorine dioxide available for use in a few niche oral care mouthwashes and toothpastes, which strive to control bad breath by destroying the bacteria that causes bad breath. Examples of these commercial oral uses are CloSYS® oral rinse and toothpaste, DioxiRinse™ mouthwash, DioxiBrite™ toothpaste and ultraDEX® oral rinse to name a few. The bacteria reduction asserted to occur through use of these products is also said to reduce plaque. These products also claim additional teeth whitening effects due to the oxidation of dental stains by chlorine dioxide. Chlorine dioxide containing toothpastes and mouth rinses may marginally lessen the rate of tartar build up by destroying bacteria and plaque. But neither chlorine dioxide by itself nor any commercially available formulations are effective in removing tartar from teeth. Instead, they have been found to be ineffective in removing tartar.

Accordingly, there has been a long-felt but unmet need for a product or method that allowed an individual to actively remove accumulated tartar and plaque from one's teeth between professional cleanings.

SUMMARY

In an aspect, the invention relates to an oral care formulation comprising at least one dianydrohexitol and at least one of active chlorine dioxide or stabilized chlorine dioxide.

In an aspect, the invention relates to an oral care formulation comprising at least one of DMI, one or more equivalents of DMI, or one or more analog of DMI in combination with at least one of active chlorine dioxide or stabilized chlorine dioxide.

In an aspect, the invention relates to a method for treating tartar on fillings, crowns, dental appliances, or teeth or adjacent to gums of a subject. The method comprises applying an oral care formulation comprising at least one dianydrohexitol and at least one of active chlorine dioxide or stabilized chlorine dioxide to at least one of the fillings, crowns, dental appliances, teeth, gums, or oral cavity of the subject.

In an aspect, the invention relates to a method for treating tartar on fillings, crowns, dental appliances, or teeth or adjacent to gums of a subject. The method comprises applying an oral care formulation comprising at least one of DMI, one or more equivalents of DMI, or one or more analog of DMI in combination with at least one of active chlorine dioxide or stabilized chlorine dioxide to at least one of the fillings, crowns, dental appliances, teeth, gums, or oral cavity of said subject.

In an aspect, the invention relates to a method for inhibiting the formation of tartar, bacteria, plaque, biofilm and periodontal disease in the oral cavity of a subject. The method comprises applying an oral care formulation comprising at least one dianydrohexitol and at least one of active chlorine dioxide or stabilized chlorine dioxide to the at least one of the teeth, gums, or oral cavity of the subject.

In an aspect, the invention relates to a method for inhibiting the formation of tartar, bacteria, plaque, biofilm and periodontal disease in the oral cavity of a subject. The method comprises applying an oral care formulation comprising at least one of DMI, one or more equivalents of DMI, or one or more analog of DMI in combination with at least one of active chlorine dioxide or stabilized chlorine dioxide to at least one of the teeth, gums, or oral cavity of the subject.

In an aspect, the invention relates to a method for preparing an oral care formulation an oral care formulation comprising at least one dianydrohexitol and at least one of active chlorine dioxide or stabilized chlorine dioxide. The method comprises forming the active chlorine dioxide immediately before use of the oral care formulation by mixing a composition comprising the stabilized chlorine dioxide and pH stabilizers with a separate composition comprising a weak acid. The method may further comprise mixing the active chlorine dioxide with at least one of the at least one dianydrohexitol or water before or during use of the oral care formulation.

In an aspect, the invention relates to a method for preparing an oral care formulation an oral care formulation comprising at least one of DMI, one or more equivalents of DMI, or one or more analog of DMI in combination with at least one of active chlorine dioxide or stabilized chlorine dioxide. The method comprises forming the active chlorine dioxide immediately before use of the oral care formulation by mixing a composition comprising the stabilized chlorine dioxide and pH stabilizers with a separate composition comprising a weak acid. The method may further comprise mixing the active chlorine dioxide with at least one of water and the at least one of DMI, one or more equivalents of DMI, or one or more analog of DMI before or during use of the oral care formulation.

BRIEF DESCRIPTION OF THE DRAWINGS

The following detailed description of embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIGS. 2A-2E illustrate progression of maladies from healthy teeth and gums to advanced periodontitis. FIG. 2A illustrates healthy teeth and gums. FIG. 2B illustrates gingivitis. FIG. 2C illustrates early periodontitis. FIG. 2D illustrates moderate periodontitis. FIG. 2E illustrates advanced periodontitis.

DETAILED DESCRIPTION

Figure 1A:
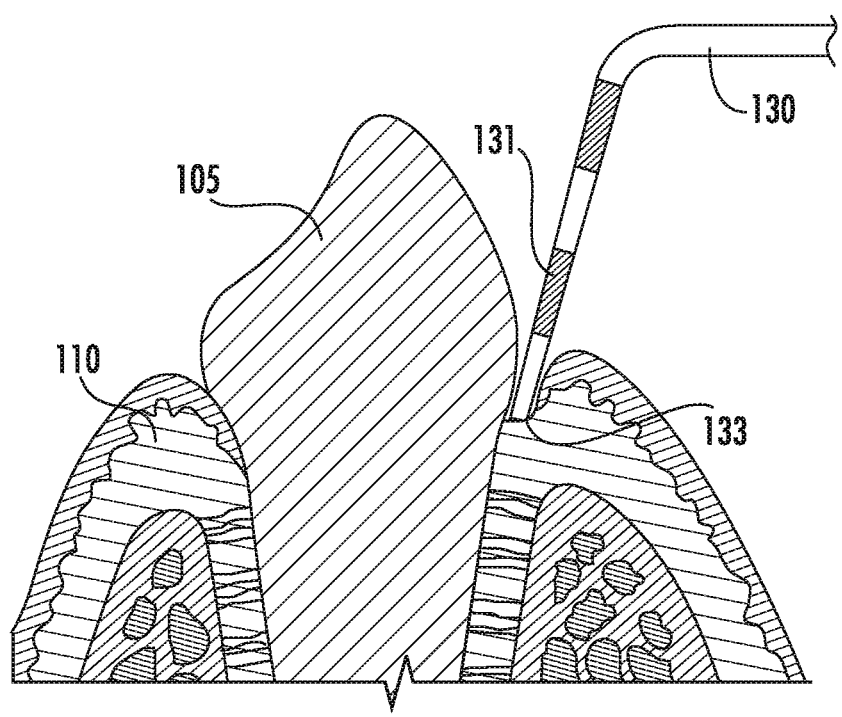
FIG. 1A illustrates gum pocket depth measurements around healthy gums.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. A number of terms are defined below.

The term, "teeth," refers to natural teeth and any other hard surfaces, such as crowns, caps, fillings, bridges, dental implants, and the like, that are fixed within the oral cavity and cleansed in situ within the oral cavity of a subject.

The terms "tartar" and "calculus" refer interchangeably to mineralized dental plaque and/or biofilms.

The terms "equivalent" and "equivalents" refer to certain compounds related to dimethyl isosorbide (DMI) that have some similar chemical properties, which may be substituted for some or all of the DMI in the embodiments. An equivalent may be isosorbide; methyl isosorbide (MI); isomannide; methyl isomannide; dimethyl isomannide; isoidide; methyl isoidide; dimethyl isoidide; isodulcide; methyl isodulcide; or dimethyl isodulcide. An equivalent may also be selected from ethers, polyethers, and polyols. The polyols may include at least one of the following: erythritol, xylitol, arabitol and ribitol, and their mono methyl; dimethyl; and trimethyl ethers. A polyol may be present alone or as mixtures of with at least one of other polyols or their mono anydro cyclic ethers. Mono cyclic anhydro ethers that may be in combination with one or more polyol may be but are not limited to 1,4-anhydroerythritol, 1,4-anhydrothreitol, 1,5-anhydroxylitol, 1,4-anhydroxylitol, 1,4-anhydroarabitol, 1,5-anhydroarabitol, 1,4-anhydroribitol, or 1,5-anhydroribitol. The mono anhydro cyclic and di anhydro cyclic ethers can also be compounds where at least one of the poly alcohol functionalities (R—OH) can remain as an alcohol (R—OH) or can be replaced with methyl ethers (R—OCH$_3$), ethyl ethers (R—OC2H$_5$), or isopropyl ethers (R—OCH(CH$_3$)$_2$).

The term "analog" of DMI refers to a glucan network expander that is predicted by the method of Example 4.

The term "effective amount" refers to an amount of an agent or agents (e.g., anti-tartar agent or agents) high enough to significantly improve the condition to be treated. A significant improvement for a method herein includes a change in tartar structure to the point where it can be removed from accessible locations of the oral cavity by brushing with a toothbrush twice each day. The change may be a softening of the consistency of the tartar. The change may be to tartar in at least one of subgingival or supragingival locations.

The term "oral care formulation" refers to a topical composition that, in the ordinary course of usage, is not intentionally swallowed for purposes of systemic administration of particular agents, but is rather retained in the oral cavity for a time sufficient to contact exposed dental surfaces and/or oral tissues for purposes of oral activity. The oral care formulation may be in the form of a solution, toothpaste, dentifrice, topical oral gel, mouth rinse, mouthwash, denture treatment product, mouth spray, lozenge, oral tablet, floss, or chewing gum.

The term "orally acceptable carrier" or "pharmaceutically acceptable excipient" refers to a suitable vehicle, which can be used to apply the present oral care formulation to the oral cavity in a safe and effective manner. Such vehicles may include materials such as fluoride ion sources (also known as fluoride providing compounds), additional anti-tartar agents, buffers, abrasive materials, peroxide sources, alkali metal bicarbonate salts, thickening materials, humectants, water, surfactants, titanium dioxide, flavor system, sweetening agents, stevia, xylitol, coloring agents, natural saliva, and mixtures thereof.

The term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The term "treating" means preventing, reducing, and/or removing dental tartar, thereby preventing, reducing and/or alleviating a dental disease.

The term "subgingival" means inside the gums. An oral care formulation may enter subgingival spaces or pockets, but it is understood that supragingival tartar can also be treated with an oral care formulation herein.

The terminology above includes the words above specifically mentioned, derivatives thereof, and words of similar import. The phrase "at least one" followed by a list of two or more items, such as "A, B, or C," means any individual one of A, B or C as well as any combination thereof.

Embodiments herein relate to oral care formulations and methods for treatment of dental disease in a subject by at least one of reducing, removing, or inhibiting the formation of tartar and plaque on and around the teeth and gums. Embodiments relate to an anti-tartar and anti-plaque oral care formulation that may be administered topically to the oral cavity of the subject. The oral care formulation may be a dentifrice, solution, toothpaste, gel, cream, mouthwash, spray, dental floss, chewing gum, or lozenge. The oral care formulation may be effective in removing, reducing, and preventing at least one of supragingival or subgingival tartar and plaque, but without many of the disadvantages that are typically associated with conventional treatments of dental disease.

An embodiment provides an oral care formulation. The oral care formulation may be for removing tartar. The oral care formulation may be for the treatment of a dental disease in a subject. The oral care formulation may prevent, reduce, or remove at least one of dental tartar or plaque. In an embodiment, the oral care formulation comprises the combination of at least one dianhydrohexitol compound with chlorine dioxide ($ClO_2$) in at least one of its active or stabilized forms. A stabilized form of $ClO_2$ (also referred to herein as stabilized $ClO_2$) may be a chlorite source. The chlorite source may be, for example, sodium chlorite, potassium chlorite, or calcium chlorite. A stabilized form of $ClO_2$ may be an alkali metal chlorite (for example, sodium chlorite or potassium chlorite) or alkaline earth metal chlorites (for example, calcium chlorite or magnesium chlorite). A stabilized form of $ClO_2$ in solution may comprise water and optionally pH stabilizers. The water may be purified water. In combination with a weak food, cosmetic grade acid or a plaque acids typically found in oral plaque or biofilm, the chlorite source may provide $ClO_2$. The weak food cosmetic grade acid or plaque acids may be, for example, acetic acid, formic acid, pyruvic acid, citric acid, lactic acid, sodium bisulfate, or disodium phosphate. An oral care formulation herein may further comprise a weak food or cosmetic grade acid. The dianhydrohexitol compound may be dimethyl isosorbide (DMI), an equivalent of DMI, and analog of DMI. The oral care formulation may comprise more than one dianhydrohexitol compound. The more than one dianhydrohexitol compound may comprise at least one of DMI, one or more equivalents of DMI, or one or more analog of DMI. An oral care formulation may comprise at least one of DMI, one or more equivalent of DMI, or one or more analog of DMI in combination with chlorine dioxide in at least one of its active or stabilized forms.

In an embodiment, the oral care formulation comprises DMI or an equivalent of DMI, $ClO_2$ in at least one of its active or stabilized forms, one or more pharmaceutically acceptable carriers, and optionally a weak food or cosmetic grade acid. The pharmaceutically acceptable carriers may include materials such as fluoride ion sources (also known as fluoride providing compounds), additional anti-tartar agents, buffers, abrasive materials, peroxide sources, alkali metal bicarbonate salts, thickening materials, humectants, water, surfactants, titanium dioxide, flavor system, sweetening agents, xylitol, stevia, coloring agents, natural saliva, and mixtures of two or more thereof.

An embodiment comprises a method for treating tartar and plaque using any oral care formulation herein. The method comprises applying an oral care formulation herein to the oral cavity of a subject. The subject may be any animal having teeth. The subject may be a mammal. The subject may be a feline, a canine, or a human. Applying may comprise applying an effective amount of the oral care formulation. The oral care formulation may be in the form of a solution or suspension. The solution or suspension may comprise other agents. Applying may comprise topically applying the oral care formulation to the oral cavity of the subject, particularly to at least one of the teeth or gums of a subject. The method may further comprise preparing an oral care formulation from two or more separate solutions or suspensions. Preparing may be conducted prior to or during the applying step. Preparing may comprise combining a combination of at least one dianhydrohexitol compound and $ClO_2$ in at least one of its active or stabilized forms with a weak food grade or cosmetic acid. Preparing may comprise combining a dianhydrohexitol compound with $ClO_2$ in at least one of its active or stabilized forms. Preparing may comprise combining a weak food grade, cosmetic grade acid or a plaque acid, at least one dianhydrohexitol compound, and $ClO_2$ in at least one of its active or stabilized forms in any order of addition. The dianhydrohexitol compound may be dimethyl isosorbide (DMI) or an equivalent of DMI. The oral care formulation applied may comprise more than one dianhydrohexitol compound. The more than one dianhydrohexitol compound may comprise at least one of DMI or one or more equivalents of DMI.

Embodiments of the oral care formulation herein and the method for treating tartar and plaque herein are very effective in removal of both supragingival and subgingival tartar, which may lead to reduction of dental pockets and gum disease. By removal of supragingival and subgingival tartar, embodiments herein may lead to healthier gums and the prevention of tooth loss. With treatment with an effective amount, subgingival and supragingival tartar may be reduced, not present, or not visible for days, week, months, or even years, thus precluding the need for quarterly, semi-annual or possibly annual dental checkups.

Treatment by a method herein with an effective amount of an oral care formulation may provide a clean teeth feeling after only a few days of use. Reduced swelling and redness of gum and cessation of gum bleeding may occur through treatment. Treatment with an effective amount may lead to gum pocket depth reductions equal to or greater than 1 mm after 5 months of use for more than 30% of gum pockets with depths of 3 mm or more. Treatment may result in a 90% or greater, greater than 90%, or 100% reduction in the amount of tartar. The amount of tartar may be measured by comparison of the overall quantity of labial and buccal tartar deposits at the gingival margin before and after treatment. A similar reduction in interproximal tartar may occur. Treatment may result in a change in tartar consistency from a flint like rock hard tartar mass to a soft friable mass which can be removed with non-metallic tools such as a toothbrush, stimudents, and ultrasonic scalers. Such removal may be relatively easy, compared to dental scaling. Treatment may result in the hygienist, dentist, or periodontist recommending a greater time interval for the next appointment. Treatment may result in no discomfort in the dental chair during a normal hygiene visit.

In a method of treatment herein, concentrations of agents in the oral care formulation may be adjusted to be low enough to avoid serious side effects (at a reasonable benefit/risk ratio), within the scope of sound medical/dental judgment. An upper limit on the amount of DMI, and equivalent of DMI, or an analog of DMI is not known. Chlorine Dioxide is very reactive to some amine functionality and is a small molecule that can quickly migrate through the saliva, biofilm to the surface of the skin if there is enough chlorine dioxide. Chlorine dioxide at 0.01% has been used with no reported problems. At 0.01%, 90% is consumed rapidly, about 30 seconds, and about 99% in a minute. There may be very little chlorine dioxide left at the end of a 2 minute brush cycle. However, different patients may react differently. A safe amount of an agent (e.g., anti-tartar agent or agents) may vary with the particular condition being treated, the age and physical condition of the patient being treated, the severity of the condition, the duration of treatment, the nature of concurrent therapy, and the particular vehicle from which the agent is applied. Increased concentrations of chlorine dioxide have been used with no problems. 0.02% and 0.03% chlorine dioxide may be acceptable. The chlorine dioxide concentration could be 0.1% or lower.

It was a surprising and unpredictable discovery that the combination of DMI or an equivalent of DMI and chlorine dioxide produces a synergistic effect. The combination is capable of removing accumulated tartar from the teeth and gums—something that was previously only possible through the physical scraping of the teeth and gums by a dental professional with specialized instruments.

An effective amount of an oral care formulation herein may be comprised of at least 1% (weight) of DMI or an equivalent of DMI and at least 10 parts per million by weight of chlorine dioxide. An oral care formulation herein may be comprised of at least 2% (weight) of DMI or an equivalent of DMI and at least 10 parts per million by weight of chlorine dioxide. The volume of an oral care formulation applied may be sufficient to allow coating of the subject's teeth with the oral care formulation. The volume may be sufficient to allow brushing of the subjects teeth while the oral care formulation is within the subject's oral cavity. The effective amount of an oral care formulation to be employed therapeutically for the treatment of a dental disease, or removal of tartar and plaque, may be changes based on a number of factors. The factors include, without limitation, the patient's sex, weight and age, the underlying causes of the condition or disease to be treated, and the formulation, and the potency of the active component. The level of tartar deposits on the teeth and gums is known to vary among individuals depending on variations in oral bacteria and enzyme types, age, salivary flow, salivary calcium concentration, pH and many other factors. Limited studies indicate the effective amount of DMI may be different for a person with light tartar build up versus heavy tartar build up. One study participant who normally had heavy tartar accumulation experienced some tartar build up at the 5.48% (w) level of DMI and 0.01% (w) chlorine dioxide in 94.51% (w) water. At the end of the 5.48% (w) DMI and 0.01% (w) chlorine dioxide trial, dental photographs were taken but the tartar was not removed from the teeth by the hygienist. At that point, the DMI portion of the formulation was changed to 15.1% (w). The results of a 15.1% (w) DMI and 0.0085% (w) chlorine dioxide in water 84.9% (w) trial showed that the tartar that was deposited in the earlier 5.48% (w) trial was almost completely removed with no tartar on the top teeth and minimal residual tartar on the bottom teeth. A method herein may include iterative treatments with an oral care formulation herein. After an iteration, the results may be assessed and the concentrations of DMI or its equivalents and $ClO_2$ in its active or stabilized forms may be adjusted to achieve a reduction in tartar. An effective amount of an oral care formulation herein may comprise DMI or an equivalent of DMI at a concentration ranging from 1% (w) to 90% (w) and the concentration of chlorine dioxide, in its active or stabilized form, ranging from 0.001% (w) to 0.08% (w). The DMI or a DMI equivalent in an oral care formulation herein may be present at a concentration of at least 1% (w). The concentration may be from 1% (w) to 90% (w). The concentration may be any concentration in the range 1% (w) to 90% (w). DMI or a DMI equivalent in an oral care formulation herein may be present at a concentration in a sub-range of 1% (w) to 90% (w), where the low endpoint of the sub-range is selected from any integer value from 1% (w) to 89% (w) and the high endpoint of the sub-range is selected from any integer value from 2% (w) to 90% (w). The concentration may be from 1% (w) to 30% (w). The concentration may be 5% (w). The concentration may be 15.1% (w). The concentration may be any specific value chosen from concentrations in any of the foregoing ranges and sub-ranges. When more than one DMI or DMI equivalent is present in an oral care formulation, the combined concentration of the all DMI and/or DMI equivalents in the oral care formulation may equal the values described immediately above for the concentration of DMI or a DMI equivalent in an oral care formulation herein.

The concentration chlorine dioxide, in its active or stabilized form, may be a concentration selected from 0.001% to 0.08% by weight. The concentration may be a concentration in a sub-range of 0.001% to 0.08% by weight, where the low endpoint of the sub-range is selected from any integer value from 0.001% to 0.0079% by weight, and the high endpoint of the sub-range is selected from any integer value from 0.0011% to 0.08% by weight. The concentration of chlorine dioxide in reference to stabilized chlorine dioxide is expressed as the concentration of chlorine dioxide, as can be determined by standard assays. For example, the concentration of a chlorine dioxide may be measured by exposing a composition comprising the stabilized chlorine dioxide to a WaterWorks™ Water Quality Test Strip (Chlorine Dioxide Check). This report from this method was used with formulations comprising either active chlorine dioxide or stabilized chlorine dioxide to determine the concentration of chlorine dioxide in the formulation.

An oral care formulation herein may comprise an orally acceptable carrier. The orally acceptable carrier may comprise one or more compatible solid or liquid filler diluents or encapsulating substances which are suitable for topical oral administration. By "compatible," as used herein, is meant that the components of the composition are capable of being comingled without interaction in a manner which would substantially reduce the composition's stability and/or efficacy.

An oral care formulation herein may comprise one or more carriers and/or excipients that may include the usual and conventional components of dentifrices (including non-abrasive gels and gels for subgingival application), mouth rinses, mouth sprays, dental floss, chewing gums, and lozenges (including breath mints) as more fully described hereinafter.

The choice of a carrier may be determined by the way the oral care formulation is to be introduced into the oral cavity. If a toothpaste (including non-abrasive tooth gels, etc.) is to be used, then a "toothpaste carrier" may be chosen (e.g., abrasive materials, sudsing agents, binders, humectants, flavoring and sweetening agents, etc.). Exemplary toothpaste carriers are disclosed in U.S. Pat. No. 3,988,433 to Benedict. If a mouth rinse is to be used, then a "mouth rinse carrier" may be chosen (e.g., water, flavoring and sweetening agents, etc.). Exemplary mouth rinse carriers are disclosed in U.S. Pat. No. 3,988,433 to Benedict. Similarly, if a mouth spray is to be used, then a "mouth spray carrier" may be chosen, or if a lozenge is to be used, then a "lozenge carrier" may be chosen (e.g., a candy base). Exemplary candy bases are disclosed in U.S. Pat. No. 4,083,955, to Grabenstetter et al. If a chewing gum is to be used, then a "chewing gum carrier" may be chosen (e.g., gum base, flavoring and sweetening agents). Exemplary chewing gum carriers are disclosed in U.S. Pat. No. 4,083,955, to Grabenstetter et al. If a sachet is to be used, then a "sachet carrier" may be chosen (e.g., sachet bag, flavoring and sweetening agents). If a subgingival gel is to be used (for delivery of actives into the periodontal pockets or around the periodontal pockets), then a "subgingival gel carrier" may be chosen. Exemplary subgingival gel carriers are disclosed in U.S. Pat. Nos. 5,198,220 and 5,242,910, issued Mar. 30, 1993 and Sep. 7, 1993, respectively, and both are to Damani. Carriers suitable for the preparation of oral care formulations herein are well known in the art. See, for example, U.S. Pat. No. 8,303,938, which is hereby incorporated by reference. Their selection will also depend on secondary considerations like taste, cost, and shelf stability, etc.

An embodiment comprises a medicated dental floss or toothpick for controlling, reducing, removing, or preventing tartar. The floss or toothpick comprises an oral care formulation herein. The oral care formulation may be incorporated on or in the dental floss or toothpick. The incorporated oral care formulation may be stable. The incorporated oral care formulation may be applied at the time of use. An embodiment includes a method of treating comprising applying an oral care formulation herein with a medicated dental floss or toothpick herein. The method may further comprise incorporating the oral care formulation on or in dental floss or a toothpick to form the medicated dental floss or toothpick at time of treating. A result of flossing action, the oral care formulation may be deposited to the inter-dental area of the teeth. Examples of making such floss are well known and are disclosed in, for example, U.S. Pat. No. 5,603,921.

Specific embodiments of an oral care formulations herein are presented here show that when DMI and chlorine dioxide are used in effective amounts in toothpastes, tooth gels and mouthwashes, they destroy and reduce the rate of formation of bacteria, biofilm, tartar and plaque and more importantly remove tartar that is already present on the tooth and tooth gum interface. The net effect of this synergistic relationship is a marked reduction of bacteria, biofilm, tartar and plaque and an elimination of tartar, gum irritation and gum bleeding and an overall improvement in the health and hygiene of the oral cavity.

An embodiment of an oral care formulation herein comprises a toothpaste formulation. The toothpaste formulation may comprise DMI and active chlorine dioxide combined with a basic toothpaste formulation. In an exemplary embodiment, the basic toothpaste formulation (100 g) comprises 24.3% (w) glycerin; 70% aqueous sorbitol 48.6% (w) (34.0% (w) sorbitol-dry basis, 14.6% (w) water) 2.7% (w) Zeodent 165 silica; 24.3% (w) Zeodent 116 silica, and 0.1% (w) spearmint oil. 2.6 ml of a 100 ppm chlorine dioxide solution was combined with 0.4 ml of DMI 15.1% (w) in a syringe barrel. The 3 ml of DMI-chlorine dioxide solution was then mixed with the 1.0 g of the basic toothpaste in the mouth. "Stabilized" or "active" chlorine dioxide at the 0.010% (w) level behaved similarly in this application. This formulation used a total of 6% (w) silica abrasives verses the typical toothpaste abrasive level of 50% (w). The toothpaste formulation may further comprise additional ingredients. The additional ingredients may improve taste, mouth feel, and effectiveness. Additional ingredients may comprises at least one of dental cleanser, water, solvents, stabilizers, coloring agents, flavoring agents, medicaments, astringents, detergents, polishing agents, abrasives sweeteners, gelling agents, thickeners, pigments, and other additives. The toothpaste formulation may be in the form of a paste or gel. A toothpaste formulation may be a multi-part formulation. The multi-part formulation may be a two part formulation, or a three part formulation. A two part formulation may comprise a part A and a part B. Part A may comprise 15.1% (w) DMI; 0.0085% (w) active chlorine dioxide and 84.89% (w) of distilled water. This may be prepared by mixing just prior to use 2.6 ml of 100 ppm chlorine dioxide with 0.4 ml of DMI. Part B, may be a basic toothpaste formulation. An example of a 100 g basic toothpaste formulation comprises 24.3% (w) glycerin; 70% aqueous sorbitol 48.6% (w) (34.0% (w) sorbitol, 14.6% (w) water) 2.7% (w) Zeodent 165 silica; 24.3% (w) Zeodent 116 silica, and 0.1% (w) spearmint oil. For use, a final formulation may be prepared by mixing part A and B. For example, 3 ml Part A may be mixed with 1 g of part B in the oral cavity and brushed on the teeth for 2 minutes and the fluids expelled. "Stabilized" or "active" chlorine dioxide at the 0.0085% (w) level behaved similarly in this application. This formulation used a total of 6% (w) silica abrasives verses the typical toothpaste abrasive level of 50%. The toothpaste formulation may further comprise additional ingredients.

An embodiment of an oral care formulation herein comprises a mouthwash formulation. The mouthwash formulation comprises DMI and active chlorine dioxide. In an exemplary embodiment, the mouthwash formulation was prepared by measuring and mixing the chlorine dioxide and DMI in a syringe immediately prior to use. The mouthwash formulation prepared comprised distilled 84.85% (w) water, 0.0085% (w) chlorine dioxide sourced from CDG Environmental and 15.1% (w) DMI. 3 ml of this DMI-chlorine dioxide solution may be transferred to the mouth after flossing and the teeth may then be brushed with a Sonicare toothbrush for 2 minutes. "Stabilized" and "active" chlorine dioxide at the 100 ppm level behaved similarly in this application. This formulation was used for three months with no (0%) silica or any other abrasive and showed no tartar or plaque residue at the end of the trial. A mouth wash formulation may further comprise additional ingredients. The additional ingredients may improve taste, mouth feel. Additional ingredients may comprise at least one of a dental cleanser, water, solvents, stabilizers, coloring agents, flavoring agents, medicaments, astringents, detergents, sweeteners, gelling agents, thickeners, pigments, and other additives. A mouth wash formulation maybe in the form of a liquid, paste, or gel.

An embodiment comprises a multi-part oral care formulation comprising components of an oral care formulation herein divided into at least two separate compositions supplied in at least two separate containers, one for each of the at least two separate compositions. One of the separate compositions may comprise the DMI or an equivalent of DMI. Another of the separate compositions may comprise the $ClO_2$ in at least one of its active or stabilized forms. Optionally, the weak food or cosmetic grade acid, if utilized to convert a stabilized form of $ClO_2$ to $ClO_2$, may be included in the composition comprising DMI, or in a separate container.

The multi-part oral care formulation may be a two-part oral care formulation comprising components of an oral care formulation herein divided into two separate compositions supplied in two separate containers, one for each of the two separate compositions. In this embodiment, one of the separate compositions may comprise the DMI or an equivalent of DMI. The other of the separate compositions may comprise the $ClO_2$ in at least one of its active or stabilized forms. Optionally, the weak food or cosmetic grade acid, if utilized to convert a stabilized form of $ClO_2$ to $ClO_2$, may be included in the composition comprising DMI.

Embodiments comprising a multi-part oral care formulation may allow forming the active chlorine dioxide immediately before or during use of the oral care formulation by mixing the at least two separate compositions in a container or in the oral cavity. Embodiments of a method for treating tartar and plaque herein may employ a multi-part oral care formulation and comprise forming the active chlorine dioxide immediately before or during use of the oral care formulation by mixing the at least two separate compositions in a container or the oral cavity.

In embodiments comprising a multi-part oral care formulation, a first composition in a first container may comprise at least one alkali metal chlorite (for example, sodium chlorite or potassium chlorite) and/or at least one alkaline earth metal chlorite (for example, calcium chlorite or magnesium chlorite) and pH stabilizers in water. The water may be purified. A second composition in a second container may comprise at least one of a weak acid (such as lactic acid, citric acid, sodium bisulfate, or disodium phosphate), solvents, stabilizers, and coloring agents, flavoring agents, medicaments, astringents, detergents, sweeteners, gelling agents, thickeners, coloring agents, or other additives. DMI or a DMI equivalent may comprise one or both of the first composition or the second composition, or may be in a third composition in a third container. The concentrations of agents in the separate compositions may be adjusted so that when equal proportions of the separate compositions are mixed, the oral care formulation resulting contains an effective concentration of agents. For example, in the two-part embodiment, the two separate compositions may be sufficient to generate chlorine dioxide at the 10 to 800 ppm range when the first and second parts are mixed in equal proportions. The DMI concentration in the combined compositions, the final oral care formulation, may be any concentration for this agent in an oral care formulation herein. The DMI concentration may be from 1% (w) to 90% (w). The DMI concentration may be from 1% (w) to 30% (w). Separated compositions to be mixed can take the forms of solutions, slurries, or gels. A striped toothpaste tube would be an example of this embodiment. Sodium chlorite and weak acid (or other chlorite source and weak acid pair) could be contained in separate channels within the toothpaste tube and delivered proportionately (with DMI or a DMI equivalent in either or both channels) via a divided nozzle.

Embodiments of a method for treating tartar and plaque herein may comprise at least one of the following aspects. The oral care formulation may be mixed with a liquid vehicle and applied to the teeth and gums via an orally-acceptable device, such as a toothbrush, cup, oral irrigator or sub-gingival applicator. The oral care formulation may be applied regularly to teeth and gums. The regularity may be any period found by the user to be acceptable. The regularity may be every day, every other day, from 1 to 3 times daily. Test participants, especially heavy tartar producers, have observed an improvement in the "mouth feel and cleanliness" within a week of starting to use this oral care formulation. The oral care formulation may be discharged in a rinsing process after application. Residual oral care formulation may linger in dental pockets, and may continue to dissolve tartar until dissipated or washed away.

Embodiments also relate to methods for treating a dental disease by preventing, reducing, and removing dental tartar from the teeth and gums. The method may comprise any a method for treating tartar and plaque herein. The method may comprise preparing a solution or suspension from an oral care formulation herein and applying the oral care formulation as a solution or suspension to the teeth and gums.

It should be understood that the application ranges set forth herein are exemplary only and are not intended to limit the scope of this invention. The therapeutically effective amount of the oral care formulation may vary with factors including, but not limited to, the efficacy of the composition, stability of the composition, the severity of the conditions to be alleviated, the age and sensitivity of the subject to be treated and the like, as will be apparent to a skilled artisan in the field. The amount of administration can also be adjusted as the various factors change over time.

The embodiments herein not only to methods for delivering the present compositions to the oral cavity of a human, but also to methods for delivering the composition to the oral cavity of other animals, e.g., household pets or other domestic animals, or animals kept in captivity. A method for treating tartar and plaque herein may be performed on any subject with teeth. The subject may be feline, canine, equine, or human. The subject may be a domestic animal, a wild animal, or an animal kept in captivity. A method for treating a dental disease by preventing, reducing, and removing dental tartar from the teeth and gums may also be performed on any subject with teeth. The subject may be feline, canine or human. The subject may be a domestic animal, a wild animal, or an animal kept in captivity.

For example, a method may comprise brushing a dog's mouth, teeth and/or gums with an oral care formulation herein. Another example may comprise brushing a cat's mouth, teeth and/or gums with the oral care formulation. Brushings may be repeated for a sufficient amount of time to see a benefit. The method may comprises preparing a solution or suspension comprising the oral care formulation, which may comprises at least DMI and chlorine dioxide in a pharmaceutically acceptable carrier, and applying the solution or suspension to the teeth and gums with a brush. The formulation can include flavorings, such as meat, poultry, fish, or malt.

A method of treating animals may comprise delivering an oral care formulation herein incorporated on or in a pet care product. A pet care product may be a chew or a toy. A pet care product may comprise an oral care formulation herein. The oral care formulation may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated oral care formulation may be released into the animal's oral cavity into a salivary medium, comparable to an effective brushing or rinsing. An embodiment comprises a pet care product comprising an oral care formulation herein.

A number of clinical diseases and conditions may be treated using an oral care formulation herein. Subjects who may benefit from treatment with an oral care formulation herein include those who suffer from dental plaque, dental tartar, gum disease, dental pockets, dental caries, gingivitis, or periodontitis.

An embodiment comprises a method for treating teeth or gums to reduce dental tartar. The method comprises applying to the surface of the teeth and/or gums an oral care formulation herein. Applying may comprise any conventional methods. Applying may comprise irrigating, brushing, spraying, painting, or rinsing of the oral cavity and the like.

It has been found that the oral care formulation of the present embodiments is very effective in the treatment of subgingival tartar, in addition to supragingival tartar. The subsequent reduction in subgingival inflammation provides relief to acute oral pain caused by infection. Further use of the oral formulation has been found to restore healthy gum tissue to formally inflamed gums within two weeks. In addition to oral inflammation reduction, periodontal pocket reductions have been observed. This process of pocket reduction is the result of both upper gum inflammation

EMBODIMENTS

The following list includes particular embodiments of the present invention. But the list is not limiting and does not exclude alternate embodiments, as would be appreciated by one of ordinary skill in the art.

1. An oral care formulation comprising: at least one dianydrohexitol and at least one of active chlorine dioxide or stabilized chlorine dioxide.
2. The oral care formulation of embodiment 1, wherein the at least one dianydrohexitol comprises at least one of DMI, one or more equivalents of DMI, or one or more analog of DMI.
3. The oral care formulation of any one or more of embodiments 1-2 comprising the one or more equivalents of DMI.
4. The oral care formulation of any one or more of embodiments 1-3 comprising DMI.
5. The oral care formulation of any one or more of embodiments 1-4, wherein the DMI is at a concentration of at least 1% (w) and the chlorine dioxide is at a concentration of at least 10 parts per million by weight, or wherein the DMI is at a concentration of at least 1% (w) and the chlorine dioxide is at a concentration of at least 0.001% (w).
6. The oral care formulation of any one or more of embodiments 1-4, wherein the concentration of the DMI is at a concentration from 1% (w) to 40% (w); or 1% (w) to 30% (w), and the chlorine dioxide is at a concentration from 10 to 800 parts per million by weight, or wherein the concentration of the DMI is at a concentration from 1% (w) to 40% (w), or 1% (w) to 30% (w), and the chlorine dioxide is at a concentration from 0.001% to 0.08% by weight.
7. The oral care formulation of any one or more of embodiments 1-2 comprising at least one of DMI, isosorbide, methyl isosorbide, isomannide, methyl isomannide, dimethyl isomannide, isoidide, methyl isoidide, dimethyl isoidide, isodulcide, dimethyl isodulcide, dimethyl 1,4-anhydrothreitol, dimethyl 1,4-anhydroerythritol, xylitol, trimethyl 1,4-anhydroxylitol, trimethyl 1,5-anhydroxylitol, trimethyl 1,4-anhydroarabitol, trimethyl 1,5-anhydroarabitol, trimethyl 1,4-anhydroribitol, trimethyl 1,5-anhydroribitol, diethylisosorbide, and diethylisomannide.
8. The oral care formulation of embodiment 7, wherein the at least one dianydrohexitol is at a concentration of at least 1% (w) and the chlorine dioxide is at a concentration of at least 10 parts per million by weight, or wherein the dianydrohexitol is at a concentration of at least 1% (w) and the chlorine dioxide is at a concentration of at least 0.001% (w).
9. The oral care formulation of any one or more of embodiments 7-8, wherein the at least one dianydrohexitol is at a concentration from 1% (w) to 40% (w), or 1% (w) to 30% (w), and the chlorine dioxide is at a concentration from 10 to 800 parts per million by weight, or wherein the concentration of the DMI is at a concentration from 1% (w) to 40% (w), or 1% (w) to 30% (w), and the chlorine dioxide is at a concentration from 0.001% to 0.08% by weight.
10. The oral care formulation of any one or more of embodiments 1-9 further comprising an orally acceptable carrier.
11. The oral care formulation of any one or more of embodiments 1-9 further comprising an orally acceptable carrier without abrasives.
12. The oral care formulation of any one or more of embodiments 1-11, wherein the oral care formulation is a dentifrice.
13. The oral care formulation of any one or more of embodiments 1-12, wherein the oral care formulation is a gel.
14. The oral care formulation of any one or more of embodiments 1-12, wherein the oral care formulation is a mouthwash.
15. The oral care formulation of any one or more of embodiments 1-12, wherein the oral care formulation is a dental floss.
16. The oral care formulation of any one or more of embodiments 1-12, wherein the oral care formulation is a chewing gum.
17. The oral care formulation of any one or more of embodiments 1-12, wherein the oral care formulation is a lozenge.
18. The oral care formulation of any one or more of embodiments 1-17, wherein the active chlorine dioxide is formed immediately before use of the oral care formulation by mixing a composition comprising the stabilized chlorine dioxide and pH stabilizers with a separate composition comprising a weak acid, wherein the stabilized chlorine dioxide comprises an alkaline metal chlorite.
19. The oral care formulation of any one or more of embodiments 1-18, wherein the active chlorine dioxide is formed immediately before use of the oral care formulation by mixing a composition comprising the stabilized chlorine dioxide and pH stabilizers with a separate composition comprising a weak acid, wherein the stabilized chlorine dioxide comprises alkaline earth metal chlorite.
20. A method for treating tartar on fillings, crowns, dental appliances or teeth or adjacent to gums of a subject comprising applying the oral care formulation of any one or more of embodiments 1-19 to at least one of the fillings, crowns, dental appliances, teeth, gums, or oral cavity of the subject.
21. The method of embodiment 20, wherein the subject is a mammal.
22. The method of one or both of embodiments 20 and 21, wherein the method reduces or removes tartar and optionally at least one of bacteria, plaque, or biofilm from the teeth, gums, and oral cavity of a mammal.
23. A method for inhibiting the formation of tartar, bacteria, plaque, biofilm and periodontal disease in the oral cavity of a mammal, comprising the step of applying the oral care formulation of any one or more of embodiments 1-19 to the teeth, gums, and oral cavity of said mammal.
24. A method for preparing the oral care formulation of any one or more of embodiments 1-19 comprising forming the active chlorine dioxide immediately before use of the oral care formulation by mixing a composition comprising the stabilized chlorine dioxide and pH stabilizers with a separate composition comprising a weak acid, wherein the stabilized chlorine dioxide comprises an alkaline metal chlorite.
25. A method for preparing the oral care formulation of any one or more of embodiments 1-19, wherein the active chlorine dioxide is formed immediately before use of the oral care formulation by mixing a composition comprising a stabilized and pH stabilizers with a separate composition comprising a weak acid, wherein the stabilized chlorine dioxide comprises an alkaline earth metal chlorite.
26. A mouthwash comprising DMI and stabilized chlorine dioxide. Plaque acids may activate the stabilized chlorine dioxide to its active form.

27. A mouthwash where DMI is included in Part A & Part B with Part A containing alkali or alkalis metal chlorites and Part B containing a food grade or cosmetic acid which in combination with Part A generates active chlorine dioxide. DioxiRinse® consists of two parts which when combined form active chlorine dioxide.

28. A mouthwash where DMI is contained in either part A or part B as described above and active chlorine dioxide is produced when the two components are mixed.

29. A mouthwash component where the components to form active chlorine dioxide are encapsulated in a powder or pill form or anhydrous DMI slurry or gel and active chlorine dioxide is formed when the pill, slurry or gel is exposed to water in the oral cavity. Dutrion® tablets would be an example of dry tablets that contain components which when added to water for active chlorine dioxide.

30. A toothpaste comprising DMI and stabilized chlorine dioxide. Plaque acids may activate the stabilized chlorine dioxide to its active form.

31. A toothpaste where DMI is included in part A and part B, with Part A containing alkali or alkalis metal chlorites and Part B containing a food grade or cosmetic acid. In combination with part A and part B generates active chlorine dioxide. Dioxibrite® Toothpaste forms active chlorine dioxide when part A and part B are mixed 32. A mouthwash where DMI is contained in either part A or part B as described above and active chlorine dioxide is activated when the two components are mixed.

33. A toothpaste component where the components to form active chlorine are encapsulated in a powder or anhydrous DMI slurry, paste or gel, and active chlorine dioxide is formed when the powder, slurry or gel is exposed to water in the oral cavity. Dutrion® tablets would be an example of dry tablets that contain components which when added to water for active chlorine dioxide.

34. A combination mouthwash which contains stabilized chlorine dioxide, which is activated by plaque acids and a toothpaste, gel or slurry that contains DMI. The two could be combined and used to brush the teeth.

35. A gel, paste, cream or mouthwash comprising an oral care formulation herein that is applied to the teeth and as result, tartar is reduced or removed through normal daily activities. This embodiment may be well suited to animals, but could also be used on humans.

36. An oral care formulation of or recited in any one or more of the preceding embodiments comprising water.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below. All amounts and proportions referred to herein and in the appended claims are percent by weight.

Examples herein combine DMI and chlorine dioxide in toothpastes, gels, and mouthwashes to show that these two components work to give a novel, synergistic effect in controlling bacteria, biofilm, tartar and plaque and, more significantly, these combinations have been found to remove tartar. Based on the results of experimentation with embodiments herein, the following theories were developed. Without being bound to any particular theory, it appears that chlorine dioxide functions as a fast acting antibacterial in the biofilm, at the tooth face and at the gum pores, to efficiently destroy bacteria and as a result destroy or severely weaken the protective structure of biofilm, and plaque. Trials have shown that approximately 90% of the "active" and "stabilized" chlorine dioxide is consumed within 30 seconds and more than 99.5% is consumed within 2 minutes of its introduction to the mouth either as a paste or wash. DMI may be acting as a delivery enhancer for chlorine dioxide, making it more effective in penetrating and destroying bacteria, biofilm, and plaque. Chlorine dioxide's ability to weaken or destroy the bacteria/biofilm structure may allow DMI greater access to the exposed tartar. Chlorine dioxide may be largely consumed and may destroy much of the bacteria and biofilm structure within the first 30 seconds of its introduction into the oral cavity, while DMI continues to rehydrate and remove tartar for the remaining time of exemplary 2 minute brushing cycles. Similar tartar reduction may be achieved by sequentially introducing chlorine dioxide to the oral cavity and then introducing DMI to the oral cavity. A trial of this sequential addition of chlorine dioxide and DMI showed a reduction in the formation of tartar. Methods herein may comprise sequential addition of DMI or an equivalent of DMI and chlorine dioxide in its active or stabilized forms, in either order.

DMI, because of its solubility and polarity, may interfere with and partially reverse the mineralization of tartar. This may occur by enhancing the rehydration of the exposed calcium phosphate in tartar or the tartar matrix, which would be more readily accessible due to the degradation of the protective biofilm and plaque by chlorine dioxide. The resulting rehydrated tartar structure may then be more easily removed by regular brushing with or without common varieties of toothpastes. The combination of DMI and chlorine dioxide also appears to rehydrate the tooth-tartar interface, causing residual tartar in hidden portions of the tooth surface to be easily removed in sheets, as reported by a dental hygienist who examined known test participants following application of the oral care formulations described herein.

The synergistic benefits of combining DMI and chlorine dioxide is further demonstrated by similar trials where 7.1% (w) DMI or 0.01% (w) chlorine dioxide were used separately from each other and where there was no possibility of this synergy. In those trials, this separate use of each compound resulted in a significantly greater amount of tartar buildup.

Example 1

In the following trials, the results were observed, reviewed, and photographed with a Schick intraoral digital camera by a dental hygienist and dentist who had previous knowledge of the conditions of each test participants teeth and gums.

A commercially available oral rinse containing approximately 100 ppm of stabilized chlorine dioxide as measured by WaterWorks™ Water Quality Test Strips was used in the following studies. A trial of mouthwash with 5.5% (w) DMI mixed with 0.0094% (w) of a readily available source of commercial stabilized chlorine dioxide in 94.5% (w) of water was conducted. With 5.5% (w) DMI levels in this mouthwash formulation, the tartar levels increased over previous studies at higher DMI levels. An intraoral photograph was taken of these tartar deposits. The mouthwash formulation was then changed from 5.5% DMI to 15.1% (w) DMI mixed with 0.0085% (w) of the same stabilized chlorine dioxide in 84.9% (w) water. At 15.1% (w) DMI, the pre-existing tartar levels (deposited while using 5.5% DMI) were removed, with no residual tartar on the top teeth and minimal tartar on the bottom teeth. The hygienist commented that this was the first time that she had seen a reduction of tartar levels of this magnitude with simple brushing. Dental photographs showing the buildup and reduction of tartar levels were taken by the hygienist to document these changes. In this set of mouthwash trials, the same commercially available toothpaste was used after each 30-second mouthwash rinse cycle.

In another trial, a test participant used a commercially available toothpaste containing stabilized chlorine dioxide to which 14% (w) DMI was added and mixed. This test participant used this 14% (w) DMI and 0.0086% (w) stabilized chlorine dioxide containing toothpaste combination for three months and brushed twice per day with an Oral B® electric toothbrush with a 2 minute brush cycle. At the end of three months, he and his dentist reported that "there was very light tartar and a little plaque between my teeth." This user commented "I have had very heavy tartar, which is why I get my teeth cleaned every three months." The dentist reported his gums were "the best he's ever seen them." Based on this result and a similar result from his next three months hygiene visit with his periodontist, his periodontist suggested he increase the duration of his cleaning from every 3 months to 5 months. This change in durations between cleanings will result in a net saving of approximately $300.00 per year for this individual alone.

At a low volume list price of $100.00 per Kilogram for DMI, a 14% (w) DMI containing toothpaste could add $2.80 to the price of a 7 oz. toothpaste tube. Bulk pricing for DMI could bring this cost down significantly, probably to under $2.00 per tube. Thus, in typical use, DMI could add $6 or $8 dollars to the annual cost of toothpaste. The potential cost saving for the improved oral hygiene and reduced dental visits would significantly outpace this added cost.

Another separate trial used 15.1% (w) DMI, 0.0085% (w) and 84.85% (w) water with the "active" chlorine dioxide sourced from CDG Environmental. One (1) gram of a basic toothpaste formulation was used with this DMI and chlorine dioxide mixture for 2 minutes with a toothbrush. A basic toothpaste formulation was made from a mixture of 48.6% (w) 70% sorbitol solution (35% (w) Sorbitol dry basis, 13.66% (w) water) 24.3% (w) glycerin, 24.3% (w) abrasive silica, 2.7% (w) thickening silica and 0.1% (w) of 100% natural spearmint oil flavoring. This trial eliminated all the other typical active components of toothpaste as contributors to the observed synergistic improvement of dental health and tartar reduction levels caused by chlorine dioxide and DMI. This formulation did not contain any solvents, stabilizers, coloring agents, medicaments, astringents, fluorides, detergents, polishing agents, sweeteners, gelling agents, pigments, or other additives used in most commercially available toothpastes, tooth gels, or mouthwashes. This toothpaste formulation used only humectants, thickeners, a flavoring agent, and a de minimis amount of silica abrasive. Because the amount of silica abrasive used in this formulation was so insignificant, it probably could have been excluded without affecting the results. The results of this trial showed a similar reduction in tartar levels to that observed in previous studies using stabilized chlorine dioxide and showed, unequivocally, that chlorine dioxide and DMI are all that is needed to eliminate plaque, gum inflammation, gum bleed, and any appreciable tartar build up in the accessible regions of the mouth.

Another separate trial used 15.1% (w) DMI, 0.0085% (w) active chlorine dioxide sourced from CDG Environmental and 84.85% (w) water. This trial eliminated the basic toothpaste formulation and all the other typical active components of toothpaste as contributors to the observed synergistic improvement of dental health and tartar reduction levels caused by chlorine dioxide and DMI. This formulation did not contain any solvents, stabilizers, coloring agents, medicaments, astringents, fluorides, detergents, polishing agents, sweeteners, gelling agents, abrasives, humectants thickeners, pigments, or other additives used in most commercially available toothpastes, tooth gels, or mouthwashes. The results of this trial showed a similar reduction in tartar levels to that observed in previous studies using stabilized chlorine dioxide and abrasives and showed, unequivocally, that chlorine dioxide and DMI are all that is needed to eliminate tartar, plaque, gum inflammation and gum bleeding in the accessible regions of the mouth.

Example 2

Gum Pocket Depth Improvements

It is estimated that more than 75% of Americans over the age of 35 have some form of gum disease. In its earliest stage, their gums might swell and bleed easily. At its worst, they might lose their teeth. Gum disease is broken down into two general classifications, gingivitis and periodontitis. The difference between gingivitis and periodontal disease is that in gingivitis the infectious disease attacks the connective tissue around the tooth. The bacteria release toxins in the gum pockets which trigger the infection. Cytokines cut their way through healthy tissue and release collagenase, prostaglandins and interleukin which destroy healthy connective tissue. In periodontitis the infectious disease has gone past the tissues into the supporting bone of the tooth causing tooth motility leading to permanent tooth loss if not professionally treated by a dentist.

Figure 1B:
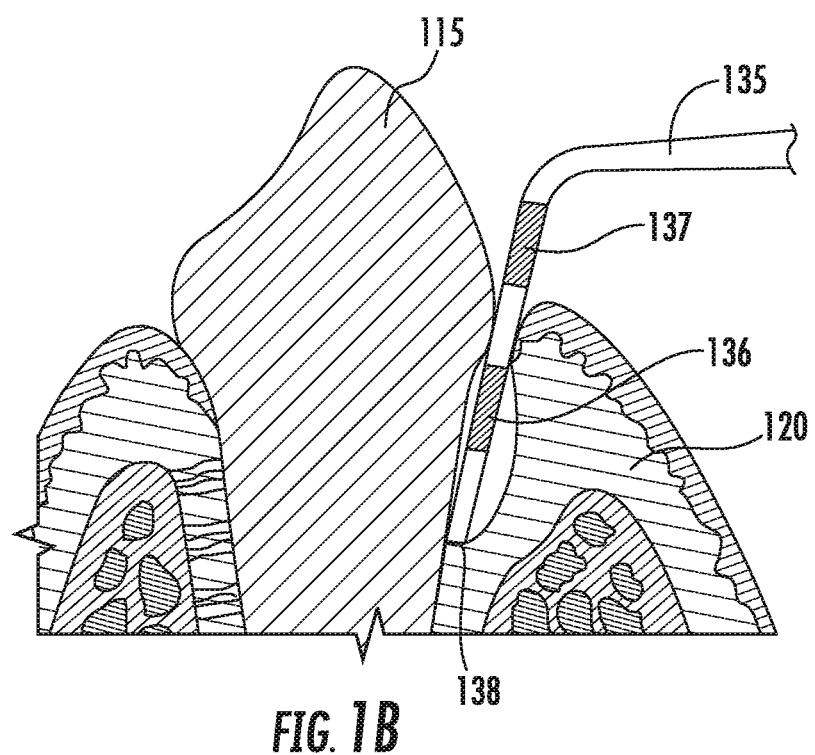
FIG. 1B illustrates gum pocket depth measurement in a periodontal pocket.

In a healthy mouth, a gum pocket can be anywhere from 1-3 millimeters deep. FIGS. 1A and 1B illustrate a method that a hygienist or dentist uses a periodontal probe to measure gum pocket depths. In FIG. 1A, a tooth 105 is illustrated surrounded by healthy gums 110, and in FIG. 1B, a tooth 115 is illustrated surrounded by unhealthy gums 120. A probe allows the dentist to measure, usually in millimeters, from the top of the gum pocket to the bottom of the gum pocket. The gradations on a probe are often set at 1 mm increments. Each gradation may be referred to as a depth marker. As illustrated in FIGS. 1A and 1B, the gradations on a probe 130 and probe 135 transition from light to dark. The probe 130 in FIG. 1A is not able to penetrate to the gum line even to the depth marker 131, and is stopped at the bottom of gum pocket 133. Depth marker 132 does not approach the gum 110. In contrast, the probe 135 in FIG. 1B penetrates past the depth marker 136 and almost to the marker 137 in order to reach to the bottom of gum pocket 138. The bottom of a gum pocket is the area where the tissue is connected through ligaments to the root. This measurement is taken very gently and causes no damage to the delicate gum tissue.

The recordings taken during periodontal probing are recorded onto a chart. There are 6 measurements taken for each tooth, 3 on the facial side and 3 on the tongue side. By monitoring the recordings against each other, the dentists and hygienists are able to determine if any areas are becoming progressively worse, or identify improvements where treatments have occurred.

An example of the progression in gum pocket depths is illustrated in FIGS. 2A-2E. FIG. 2A shows healthy teeth and gums; FIG. 2B shows gingivitis, FIG. 2C shows early periodontitis, FIG. 2D shows moderate periodontitis, and FIG. 2E shows advanced periodontitis. When a tooth has periodontal disease, the gum tissue becomes detached past 3 mm deep. At 1 to 3 mm deep a pocket is considered healthy, while 4 mm or deeper it is considered unhealthy. When connective gum tissue loss occurs, it is also a sign that there is bone loss. Scaling and root planing, or "deep cleaning" of deep pockets is recommended with pocket depths greater than 4 mm. Deep pocket cleaning is more involved as its focus is to remove the tartar from all pocket areas, since tartar is the bacteria's "hiding place." Diligent brushing and flossing cannot remove the tartar from a deep pocket. If left alone, these infections can cause more bone loss and tissue detachment, resulting in tooth loss.

Figure 3:
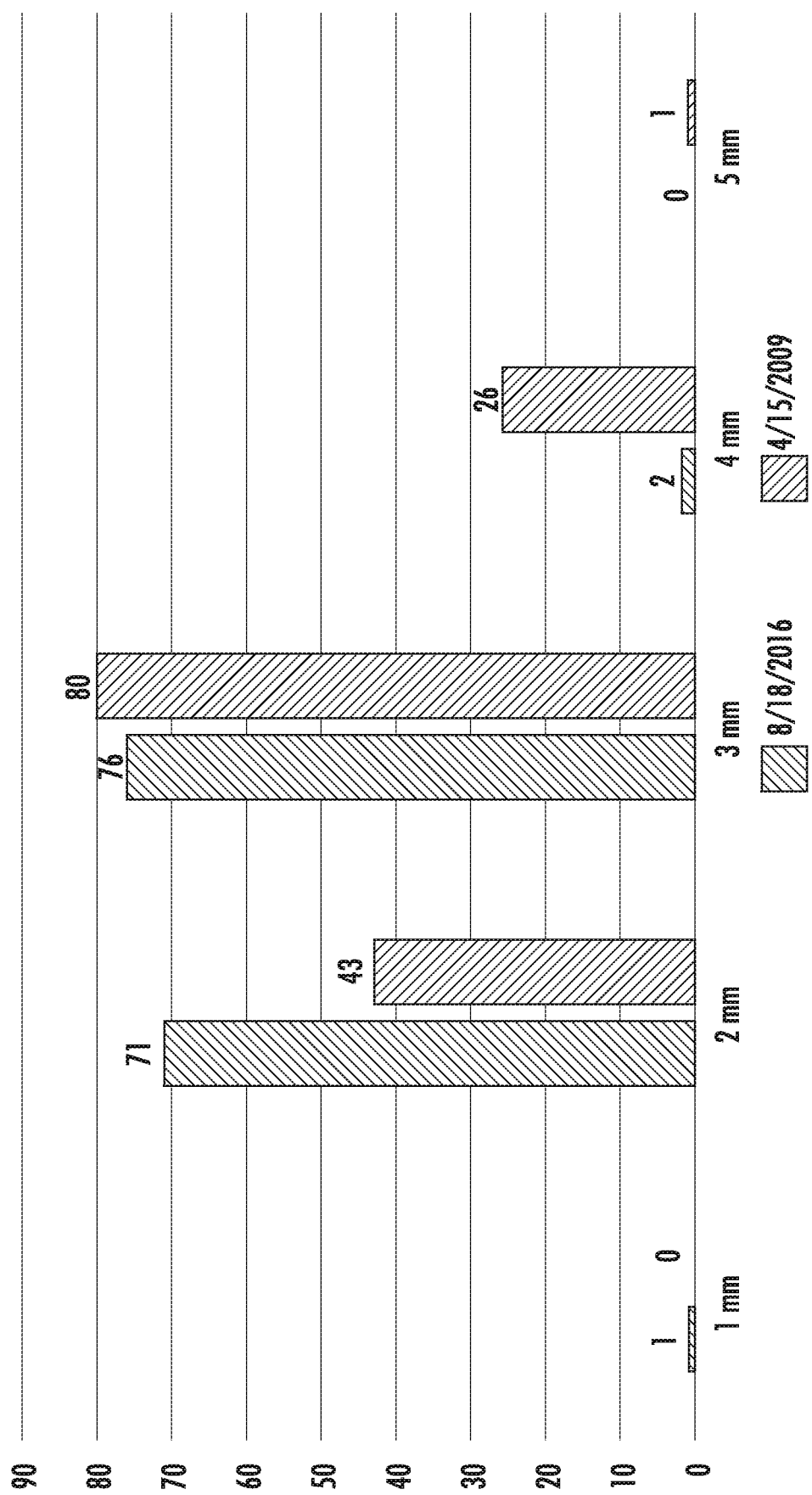
FIG. 3 illustrates reductions in gum pocket depth measurements.
Figure 4:
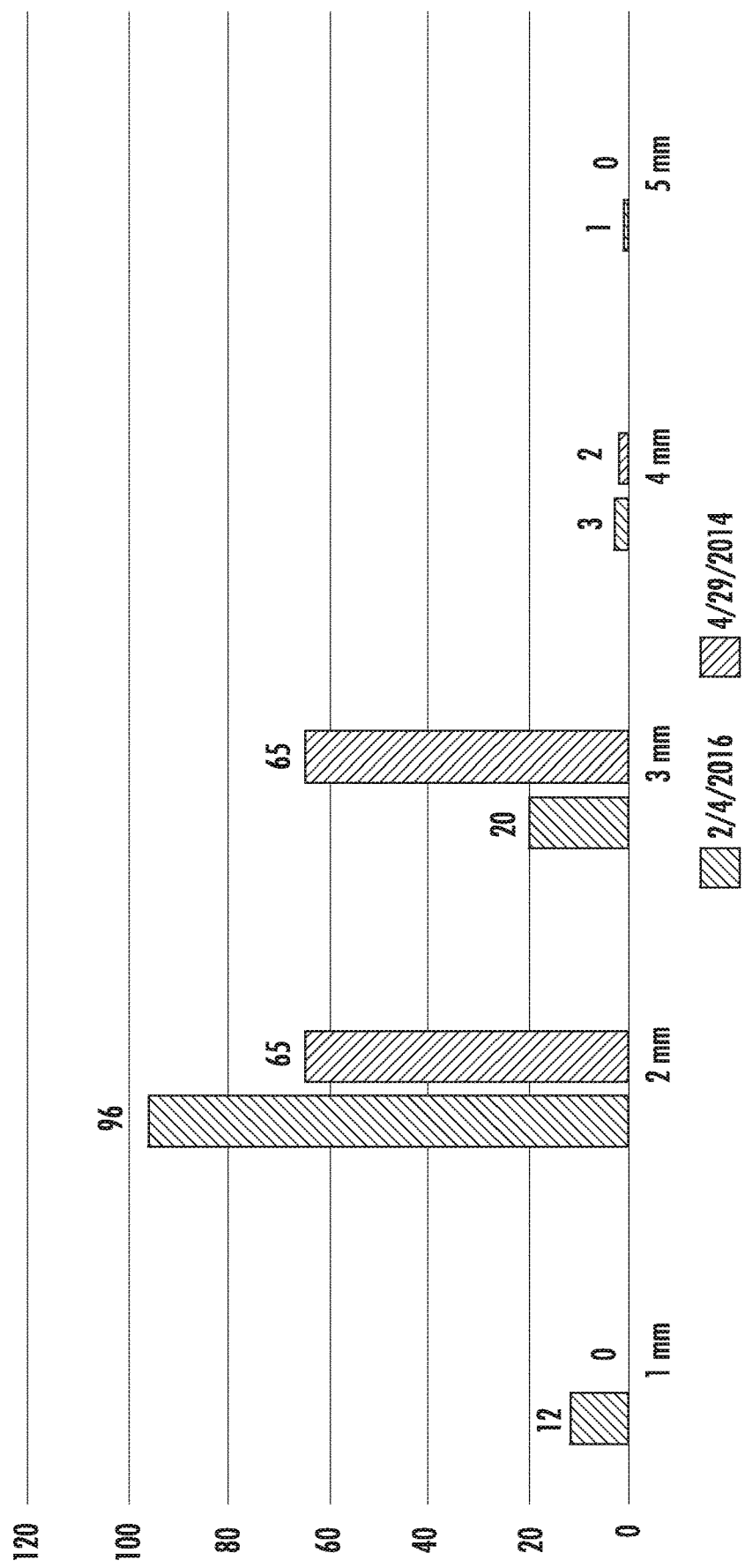
FIG. 4 illustrates reductions in gum pocket depth measurements.
Figure 5:
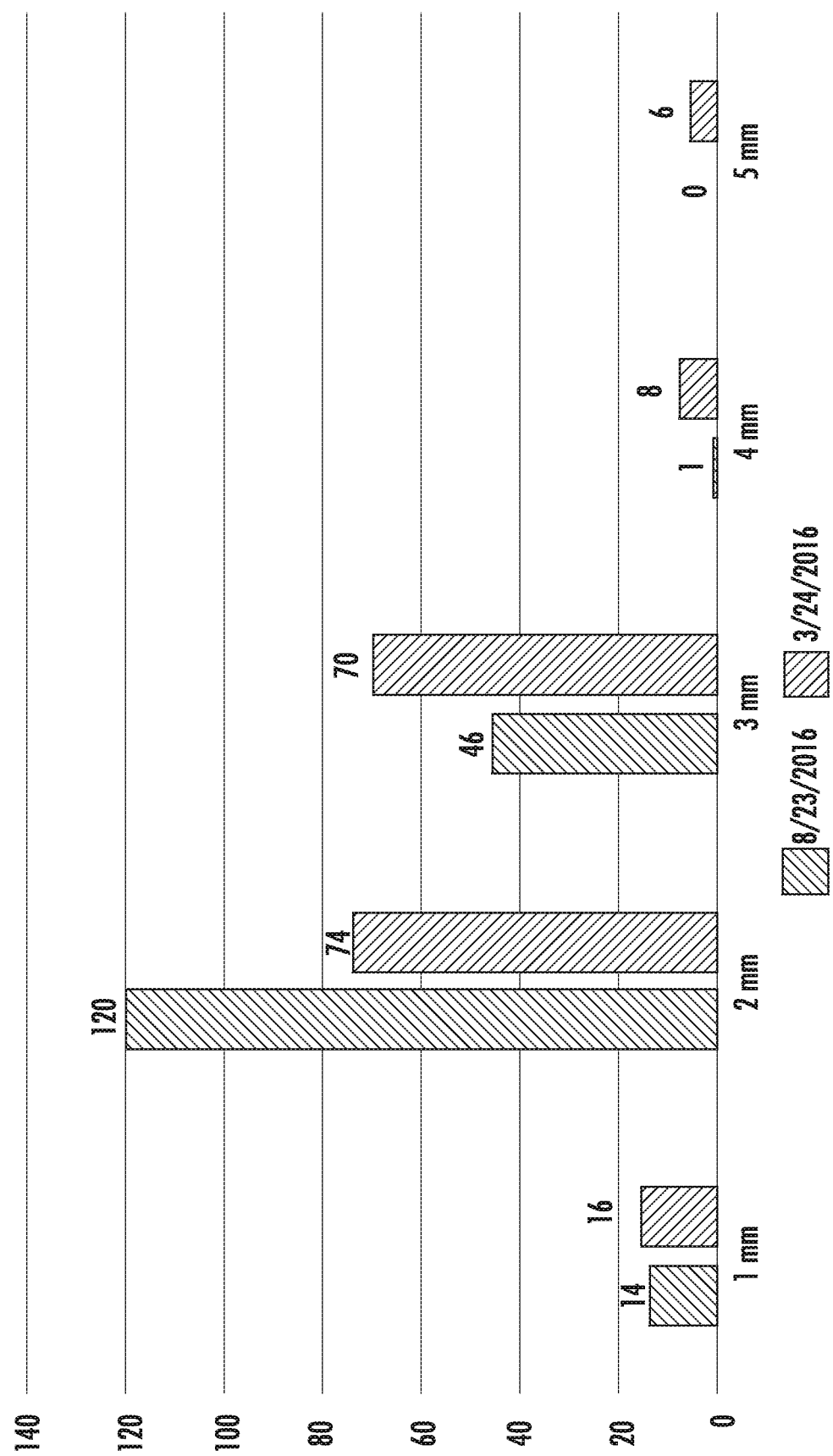
FIG. 5 illustrates reductions in gum pocket depth measurements.

The novel synergies of the formulations and methods discussed herein remove both supragingival and subgingival (periodontal pocket) tartar with 2 minute brushings twice daily. The data provided in FIGS. 3, 4, and 5 shows the dramatic and consistent reduction in gum pocket depth after only 4 and 5 months of twice daily use. In each of FIGS. 3, 4, and 5, the y-axis represents the number of gum pockets measurements at noted depth, the x-axis represents gum pocket depth.

FIG. 3 illustrates reductions in gum pocket depth measurements in a human male subject, age 63. A 40.9% reduction in gum pocket depths was observed in 5 months. The oral care formulation comprised 10% DMI and 100 ppm $ClO_2$. FIG. 4 illustrates reductions in gum pocket depth measurements in a human femal subject, age 63. A 40.9% reduction in gum pocket depths was observed in 4 months. The oral care formulation comprised 14.5% DMI and 100 ppm $ClO_2$. FIG. 5 illustrates reductions in gum pocket depth measurements for a human female subject, age 63. A 35.4% reduction in gum pocket depths was observed in 5 months. The oral care formulation comprised 12% DMI and 100 ppm $ClO_2$. This data was provided by test participants whose gum pocket depth measurements were made by different hygienists in non-related dental practices.

As shown in FIGS. 3-5, gum pocket depths of 4 and 5 mm are almost totally eliminated after only 4 or 5 months of use of DMI and chlorine dioxide in 10%, 12% and 14.5% DMI/100 ppm chlorine dioxide toothpaste formulations. The use of all three of these DMI concentrations resulted in at least 1 mm reductions in gum pocket depths for 35% or more of the gum pocket measurements.

The DMI—chlorine dioxide formulation may cleave peptide linkages as well as splaying, fragmenting and re-hydrating the insoluble glucans which provide the structural matrix (glue) that makes tartar rock hard. These actions may facilitate the fragmented colloidal tartar to harmlessly float away from the gum pocket and allow reattachment of the gum to the tooth, thereby reducing gum pocket depths and improving gum health. Examples of these gum pocket depth reductions are shown in the previous three graphs. Up until this point in time the only effective way of removing gum pocket tartar, the hiding place for bacteria, was with scaling and or root planing by a dentist or hygienist.

Example 3

Studies to Colloidal Fragmentation of Tartar

The formation of colloidal fragments from tartar by DMI and chlorine dioxide is demonstrated in the following two trials. Together DMI and chlorine dioxide fragment the insoluble glucan and polypeptide matrix which hold tartar together. Neither chlorine dioxide nor DMI by themselves show the ability to fragment the tartar matrix. Not to be held to any specific mechanism of action, it would appear that the primary role of chlorine dioxide is to break polypeptide linkages and protein polyol linkages. But this ability alone is insufficient for tartar fragmentation. The insoluble glucan matrix also appears to provide much of the needed glue to keep the tartar intact. Dimethyl isosorbide appears to enter the cracks within the insoluble glucan structure and splay out the glucan structure which in turn promotes the entry of water to re-hydrate the normally insoluble glucan and destabilize and glucan/biofilm matrix and fragment the tartar structure. Evidence for this rehydration and fragmentation mechanism is provided in the following two studies.

Centrifuge Study #1

Figure 6:
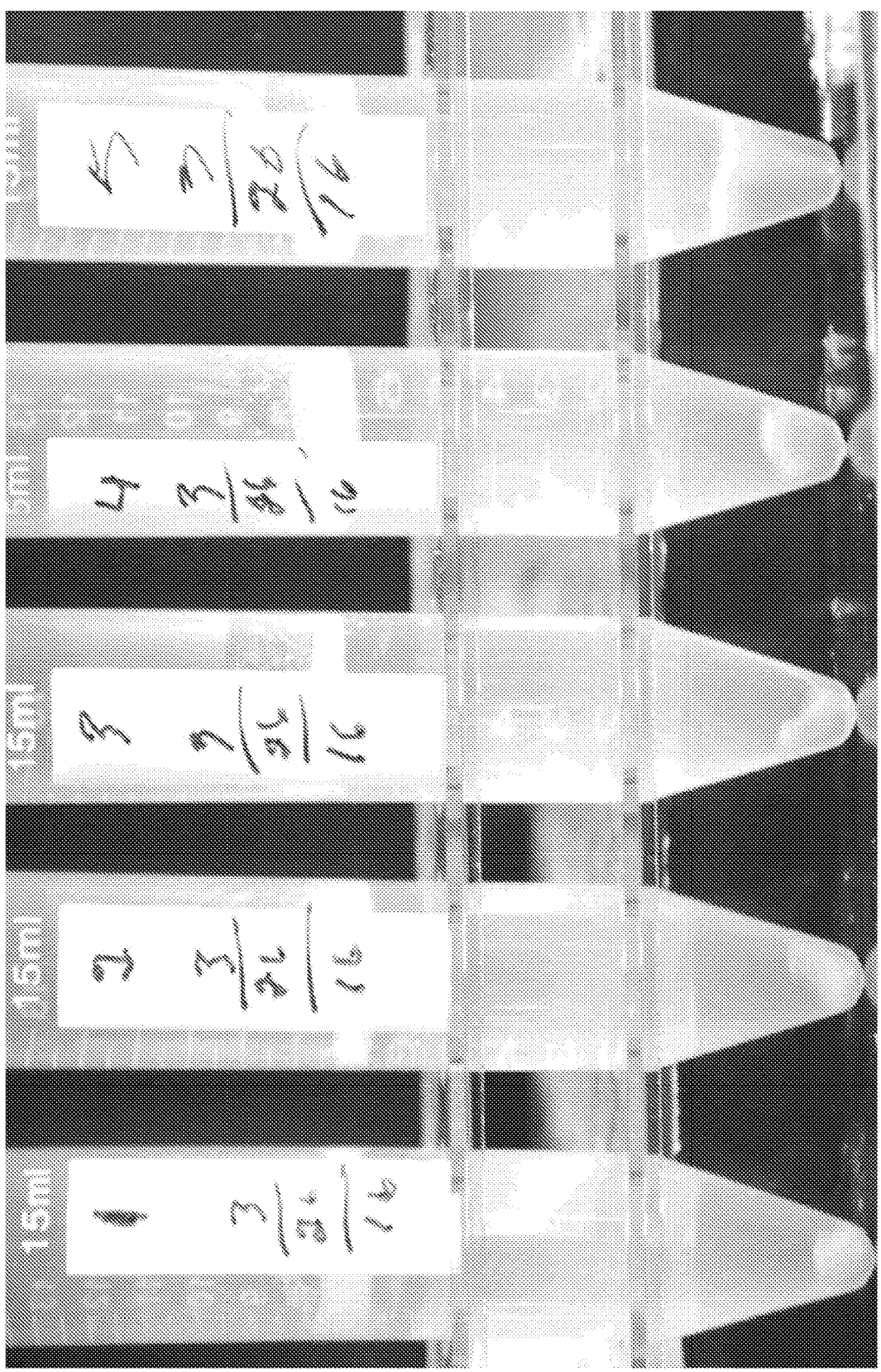
FIG. 6 illustrates removal of material from teeth before and after treatment with an oral care formulation herein.

In the first study the subject's teeth were flossed with Reach floss, then flossed with a Waterpik water flosser. After the water flossing the water was removed from the mouth. 3 ml of distilled water was added to the mouth and the teeth were brushed with only water for 2 minutes. After the 2 minutes brushing cycle, the water was expelled into a funnel into a centrifuge tube. The subject's teeth were again flossed with a water flosser and then procedure "A" was followed three more times for a total of four 2 minute brushing cycles. Each time, the brushings were expelled to a new labelled centrifuge for a total of 4 centrifuge tubes. The fifth brushing, after another Waterpic water flossing, used 0.4 ml of DMI in 2.6 ml of 100 ppm chlorine dioxide in water. The teeth were brushed with this mixture for a $5^{th}$ time and the brushings were transferred in the same fashion to a $5^{th}$ labelled centrifuge tube. The 5 centrifuge tubes were spun down in a centrifuge at a centrifuge force of 1,350 g for 5 minutes. FIG. 6 shows the results of this study.

Referring to FIG. 6, as can be seen from the sediment concentrated in the bottoms of the centrifuge tubes that the first four 2 minutes of brushing with water removed very little material, most likely soft plaque, from the teeth. But in the fifth brushing cycle, when the chlorine dioxide and DMI were used together, the fragmentation of the tartar resulted in the formation of a large amount of solids as a colloidal suspension. When this procedure was used the next day by the same subject there was very little precipitate in any of the 5 centrifuge tubes. The reason for this was there was not enough time (24 hours) to allow a measurable amount of tartar to accumulate on the teeth.

Tartar was then allowed to build on the teeth for 6 days by using a commercial tartar controlling toothpaste twice per day without using either DMI or chlorine dioxide. On the sixth day centrifuge study #2 was conducted.

Centrifuge Study #2

In this second study, the teeth were flossed with Reach floss, then flossed with a Waterpik water flosser. The water risings were removed. After the flossing water was removed, 0.4 ml of DMI in 2.6 ml of 100 ppm chlorine dioxide in water was used for the first brushing. After 2 minutes of brushing, the brushings were transfected in the same fashion as before through a funnel to a centrifuge tube. As in Centrifuge Study #1 a water flosser was used between each brushing cycle. For the next 4 brushings 3 ml of water were added to the mouth and the teeth brushed with water only for 2 minutes. After the 2 minutes, the brushings were expelled through a funnel to a centrifuge tube. The teeth were flossed with a Waterpik water flosser as before. Each time the brushings were expelled to a new labelled centrifuge for a total of 5 centrifuge tubes. The 5 centrifuge tubes were as spun down at a centrifuge force of 1,350 g for 5 minutes.

Figure 7:
FIG. 7 illustrates removal of material from teeth before and after treatment with an oral care formulation herein.

FIG. 7 shows the results of this study. As can be seen, the combination of DMI and chlorine dioxide removed copious amounts of plaque and tartar in the first brushing. The following water only brushings continued to release some tartar in diminishing quantities. The residual DMI and chlorine dioxide in the remaining tartar on the teeth were still facilitating fragmentation and rehydration of the insoluble glucan matrix.

Example 4

Virtual Binding Assay for Glucan Network Expanders

The insolubility of branched (1-3)-α-D glucans that are a major component or oral biofilms are thought to be due to the stabilizing effect that the branches have on helical conformations of the glucan backbone which in turn pack tightly into insoluble glucan networks in tartar. On this basis, compounds that can disrupt the stabilizing influence of the side chains on the helical structures could be good candidates for expanding and fragmenting glucan networks. This could then increase the permeability of the glucan network to water and biological control agents. The virtual assay described below computationally tests the ability of candidate glucan network expanders to bind in the U-shaped pockets formed by neighboring side chains that extend from a helically twisted glucan backbone that branches at every other glucose unit. Effective binding to these pockets could correlate with network expansion and fragmentation.

Structures of Candidate Glucan Network Expanders

Figure 8:
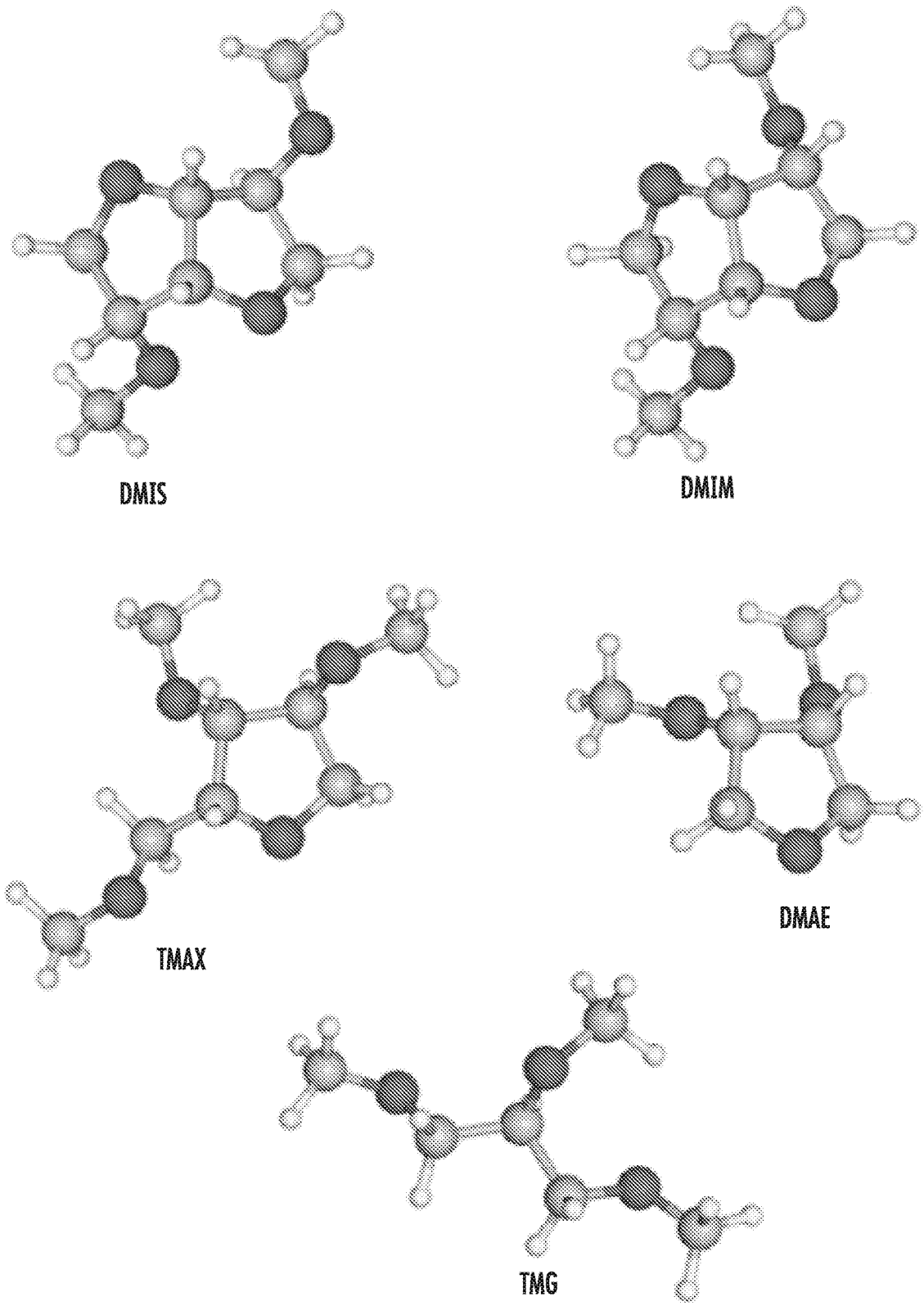
FIG. 8 illustrates optimized structures of five of the glucan network expanders.

The geometries of six possible glucan network expanders (GNEs) were first optimized using the Fletcher-Reeves optimizer as implemented in the HyperChem molecular modeling system. Energies and forces were calculated using either the semi-empirical AM1 electronic structure method, or a CHARMM molecular mechanics force field. The optimized structures of five of the glucan network expanders are shown in FIG. 8. The five are: dimethylisosorbide (DMIS), dimethylisomannide (DMIM), trimethylanhydroxylitol (TMAX), dimethylanhydroerythritol (DMAE), and trimethylglycerol (TMG). The structure of a sixth network expander, diethylisosorbide (DEIS), which is closely related to the dimethylisosorbide (DMIS) is not shown. For reference purposes, the structure of the all carbon analog of DMIS, diethyloctahydropentalene (DEOHP) was also optimized in the same manner.

Structure of Model Glucan Target

Figure 9:
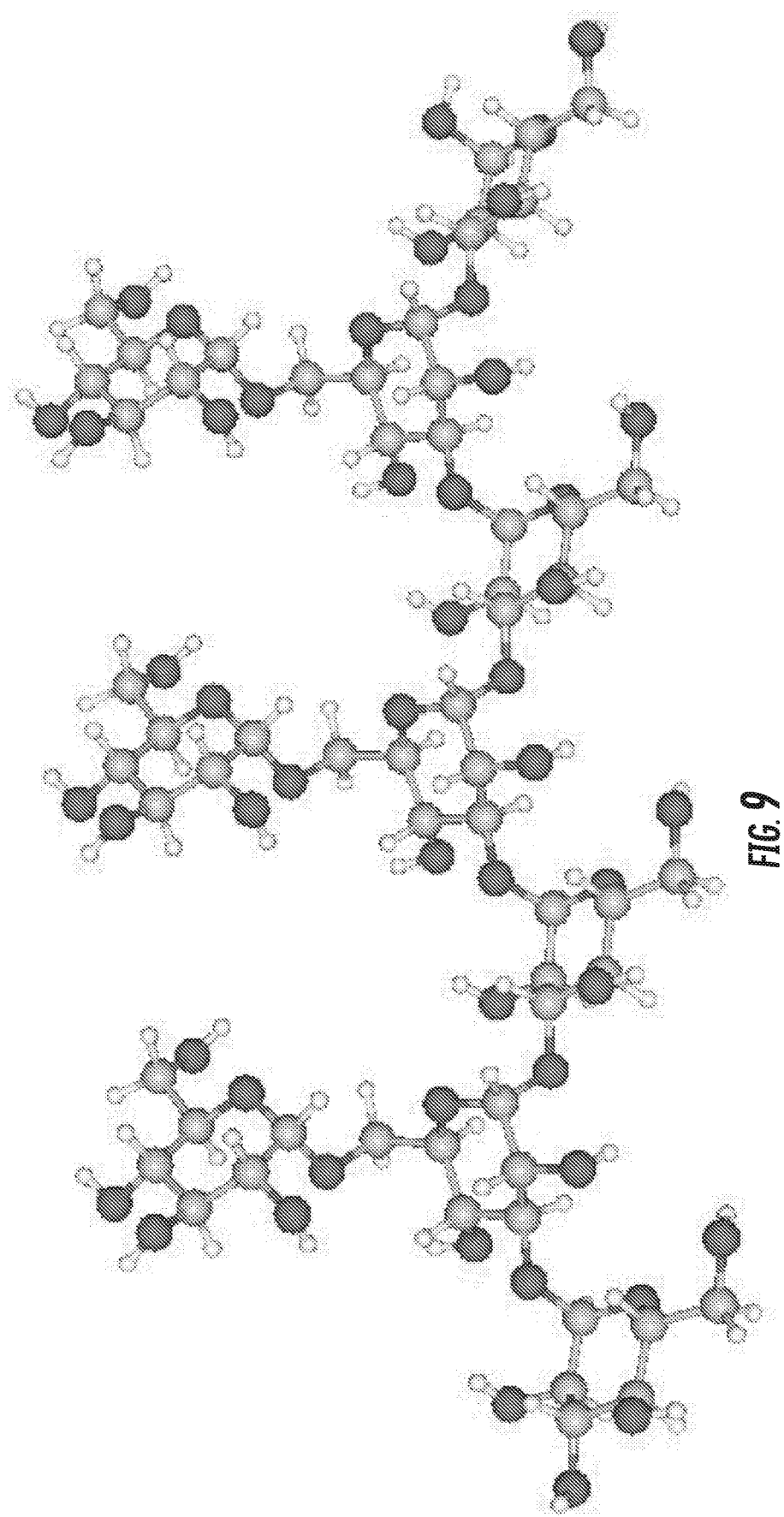
FIG. 9 illustrates 2,4,6-branched glucan heptamer, -(αDGlc(1-3)αDGlc(1-3) [(1-6)αDGlc])3αDGlc-.

The 2,4,6-branched glucan heptamer, -(αDGlc(1-3)αDGlc(1-3)[(1-6)αDGlc])3αDGlc-, which we use as a model target for the GNEs, is illustrated in FIG. 9. The conformation shown and used was obtained by fully extending the backbone of the heptamer, and then optimizing the structure using the same methods as described above for the GNEs. The resultant conformation resembles a comb with three tines, and the site used for the virtual binding assay was the pocket between the first and second tine.

Binding Energies for Glucan Network Expanders to Glucan Target

Binding energies, $\Delta E_{bind}$, at 0 K for the glucan network expanders (GNEs) to the model 2,4,6-branched glucan heptamer were obtained by taking the difference in product and reactant energies for the following reaction.

GNE+Glucan→GNE–Glucan

The structures of the reactants and products were optimized using the Fletcher-Reeves conjugate gradient method with a termination condition of 0.5 kcal/Å mol. Starting structures for the GNE-Glucan complexes were determined by first manually docking the GNE into the binding pocket to avoid steric clashes and to align for potential hydrogen bonds. Table 1 summarizes the results. The $\Delta E_{Bind}$ values reported in the AM1 column were calculated using energies for reactants and products whose geometries had been optimized at the AM1 level of approximation. The $\Delta E_{Bind}$ values reported in the CHARMM column were calculated using energies for reactants and products whose geometries had been optimized using the CHARMM molecular mechanics force field with a distance dependent dielectric constant. To locate alternative binding modes for the GNE-glucan complex with possibly lower energy, molecular dynamics simulations were then run for a period of 1 picosecond at 300 K, and the resultant structures reoptimized. In most cases a lower energy binding mode was located by this procedure. Table 1, below, reports binding energies for GNEs.

TABLE 1

| Binding Reaction | $\Delta E_{bind}$/(kcal mol$^{-1}$) | |
|---|---|---|
| | AM1 | CHARMM |
| DMIS + glucan → DMIS-glucan | −27.1 | −20.22 |
| DEOHP + glucan → DEOHP-glucan | −19.5 | −9.77 |
| DMIM + glucan → DMIM-glucan | −23.6 | −11.26 |
| TMAX + glucan → TMAX-glucan | −25.6 | −2.94 |
| DMAE + glucan → DMAE-glucan | −25.5 | −21.15 |
| DEIS + glucan → DEIS-glucan | −29.5 | −17.94 |
| TMG + glucan → TMG-glucan | −25.0 | −12.37 |

Structures of glucan network expander (GNE)-Glucan Target Complexes.

Figure 10:
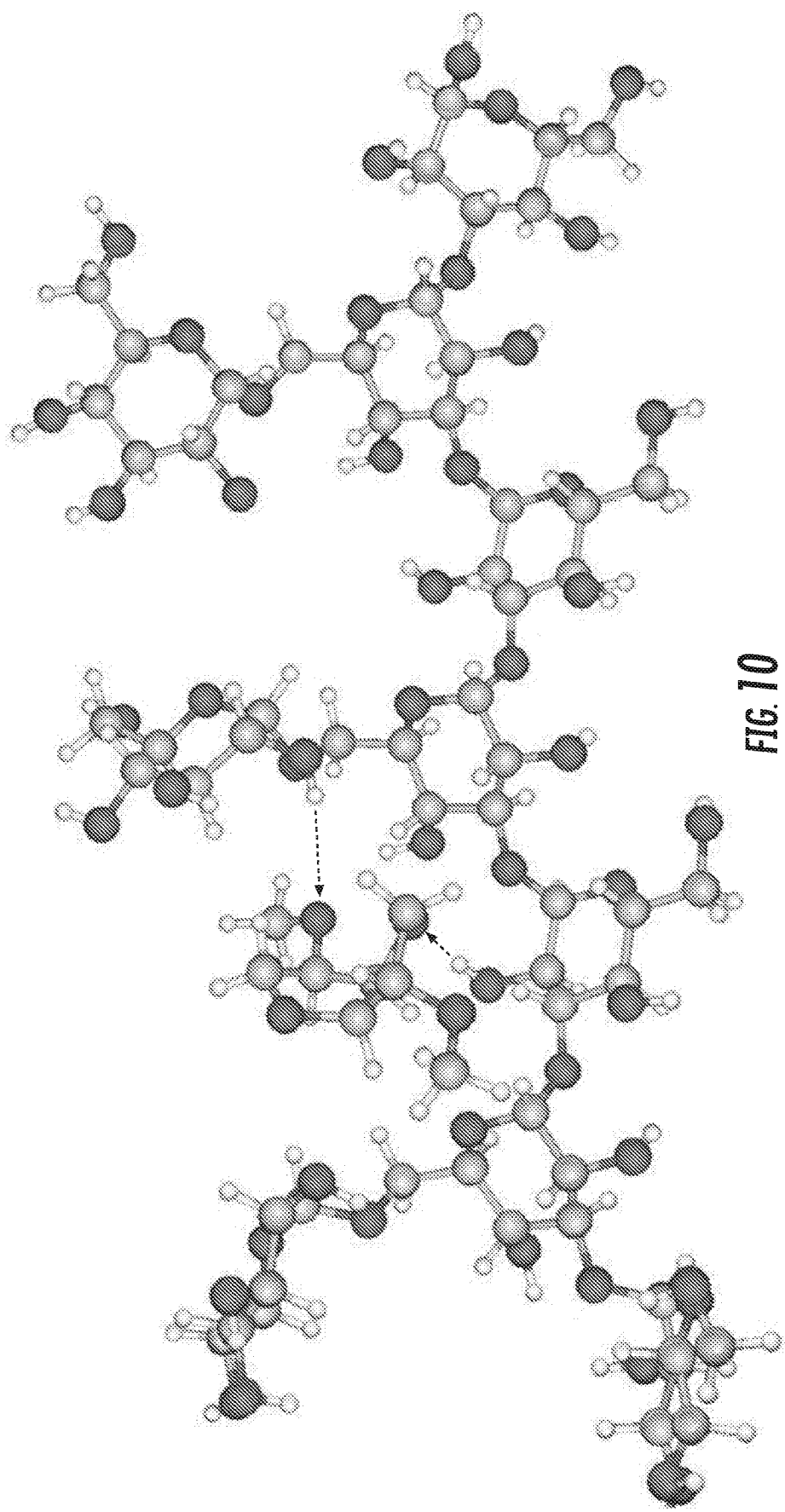
FIG. 10 illustrates the structure of a complex between dimethyl isosorbide (DMIS) and a model glucan target.

The structure for the dimethyl isosorbide (DMIS)-glucan complexes as determined using the CHARMM method is shown in FIG. 10. In FIG. 10, DMIS is docked into the pocket between the terminal and middle glucos-1-yl side chains of the 2,4,6-branched glucan heptamer. Hydrogen bonds between DMIS and middle glucosyl side chain, and between DMIS and third glucosyl unit of the backbone are shown with dashed arrows. The binding of the DMIS induces a conformational change in which the glucosyl side chains have splayed to accommodate the DMIS (compare FIGS. 9 and 10). The relatively rigid DMIS exhibits good shape complementarity to the binding pocket after the induced conformational change. Two stretched hydrogen bonds are evident, one donated by a hydroxyl group of a glucosyl side chain to the oxygen of a methoxy group of the DMIS, and the other from a hydroxyl group of a backbone glucosyl unit to the oxygen in one of the tetrahydrofuran rings. Similar calculations were repeated for complexes of DMIM, TMAX, DMAE, DEIS, and TMG with the target, as well as for DEOHP, the all carbon analog of DMIS. A pair of hydrogen bonds analogous to those formed by DMIS was observed in the model for each of the complexes formed by DMIM, TMAX, DMAE, DEIS and TMG with the 2,4,6-branched glucan heptamer. Based upon $\Delta G_{Bind}$ values, DMI, followed closely by DEIS, bound most strongly in the model glucan binding pocket. DMAE also appears to have an advantage over DMIS as a GNE but entropic factors would seem to lower this advantage. But both may are equivalents for DMI.

Free Energy of Binding Calculations

Free energies and entropies of binding for the GNEs were calculated using the CHARMM molecular mechanics force field with a distance dependent dielectric constant as implemented in the HyperChem molecular modeling system. After geometry optimization as described above, the frequencies from a vibrational analysis were used in standard statistical mechanical expressions to calculate entropies and free energies at 298 K. The binding free energies and entropies as calculated from the differences in these thermodynamic properties for products and reactants are listed in Table 2, below.

TABLE 2

| Binding Reaction | $\Delta G_{Bind}$/ (kcal mol$^{-1}$) | $\Delta S_{Bind}$/ (kcal K$^{-1}$ mol$^{-1}$) |
| --- | --- | --- |
| DMIS + glucan → DMIS-glucan | −0.95 | −0.049362 |
| DEOHP + glucan → DEOHP-glucan | 7.14 | −0.075714 |
| DMIM + glucan → DMIM-glucan | 10.82 | −0.068345 |
| TMAX + glucan → TMAX-glucan | 18.03 | −0.061589 |
| DMAE + glucan → DMAE-glucan | 10.81 | −0.074826 |
| DEIS + glucan → DEIS-glucan | 1.33 | −0.051774 |
| TMG + glucan → TMG-glucan | 13.81 | −0.053530 |

Entropies of binding, $\Delta S_{Bind}$, are naturally negative due to losses of translational, rotational, and vibrational freedom upon binding, but the differences in $\Delta S_{Bind}$ between molecules are largely due differences in reductions in vibrational freedom. Specifically, binding is expected to restrict internal rotations about exocyclic bonds for some GNEs more than for others.

Based upon $\Delta G_{Bind}$ values, DMIS, followed closely by DEIS, binds most strongly to the model glucan binding pocket. The difference in the binding free energies of DMIS and DEOHP (8.09 kcal mol$^{-1}$) is consistent with the formation of two intermolecular hydrogen bonds by DMIS that are not possible for its all hydrocarbon analog, DEOHP. Based upon the calculations at 0 K reported in Table 1, DMAE appears to have an advantage over DMIS as a GNE. However, when entropic considerations are considered, DMAE falls into the pack of GNEs predicted to be less effective. An examination of the DMAE-glucan structure reveals that the DMAE is completely buried in the pocket of the glucan with four C—O bond rotations in the two methoxy groups significantly restricted. On the other hand, only one of the DMIS methoxy groups is buried in the glucan pocket in the DMIS-glucan complex. The buried methoxy group accepts a hydrogen bond that restricts two internal C—O bond rotations, but the second methoxy group projects out of the pocket so that its rotation is still relatively unhindered upon binding.

DMIM, TMAX, DMAE, and DEIS are referred to herein as equivalents of DMI. An analog of DMI may be predicted by using the at least one of the model, tests, or calculations as in this example. An analog would have similar properties as the compounds tested above.

Example 5

Tartar removal and periodontal Gum pocket reduction with non-abrasive brushing with dimethyl isosorbide and chlorine dioxide.

All photographs in this example were taken by a professional oral hygienist using a Schick intraoral digital camera.

Each minute of each day, saliva is being created in our mouths. This saliva contains varying amounts of calcium and phosphate ions, bacteria and other components in a water solution. Over time bacteria colonies grow in number and use carbohydrates to produce a protective layer called biofilm. This combination of materials lose water (dehydrate) over time and form plaque which with additional time hardens to form rock hard tartar.

This tartar formation process can be interrupted by using mouthwashes or toothpastes that destroy bacteria and remove plaques. But between each of these interruptions by a mouthwash or a toothpaste, the process of tartar formation continues. The rate of tartar formation varies from individual to individual because of differences in saliva flow, the concentration of calcium and phosphate ions and many other personal factors. Mathematically one could look at this process as an equation where $T_{24\ hour}=K \times P$ where the $T_{24\ hours}$ is the tartar amount formed over a 24 hour period and it is related to K where K is a tartar formation constant and where P is a variable factor based on a combination of personal factors such as saliva formation rate and the concentration of calcium and phosphate ions, pH, bacteria and saccharide sources and concentrations.

Figure 11:
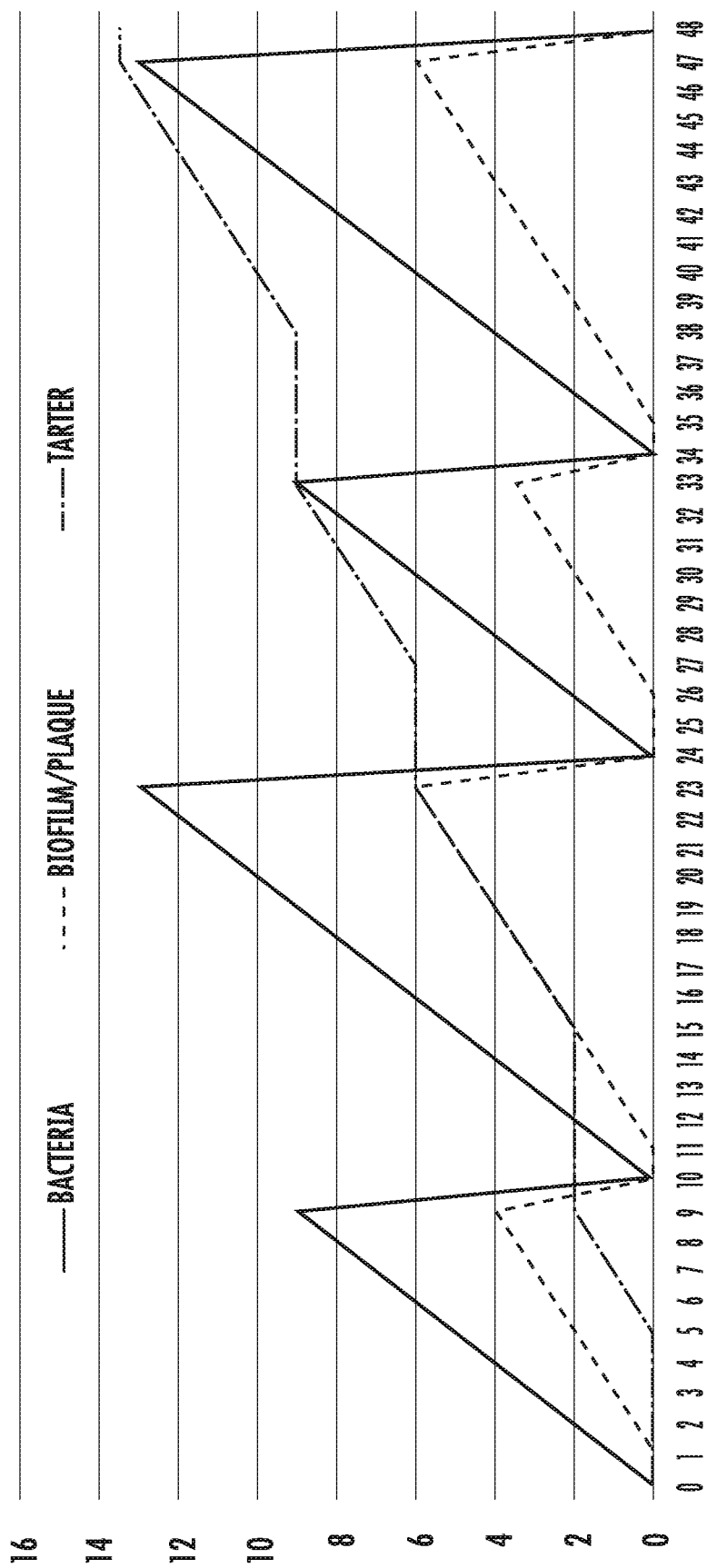
FIG. 11 illustrates a representation of a tartar formation timeline.

A representation of a tartar formation timeline is conceptually depicted in FIG. 11. The graph assumes a professional cleaning at time "0" (8:00 AM) and the flossing and brushing of teeth after dinner at 6:00 PM (10 hours after cleaning) and again after breakfast at 8:00 AM (24 hours) and the cycle continuing onwards. This conceptual graph assumes all the plaque and bacteria are removed at each flossing/brushing cycle and that tartar, which cannot be removed by brushing, remains on the tooth surface. The graph parallels the actual experience of most individuals with some level of tartar formed each day with that amount varying with each individual.

There are many toothpastes on the commercial market that claim to "inhibit the formation of tartar" or "fight tartar by reducing plaque." But no commercial toothpastes claim the ability to remove tartar once it has formed. In contrast, the oral care formulations and methods herein have been shown to remove tartar after it has formed. One popular tartar-inhibiting toothpaste, CloSYS® Sulfate-Free Fluoride Toothpaste, claims to kill 99.9% of germs that cause bad breath, dissolve unwanted compounds and reduce harmful bacteria in your mouth. It also claims "Anti-Plaque/Anti-Cavity" characteristics, but it does not remove tartar.

Figure 12:
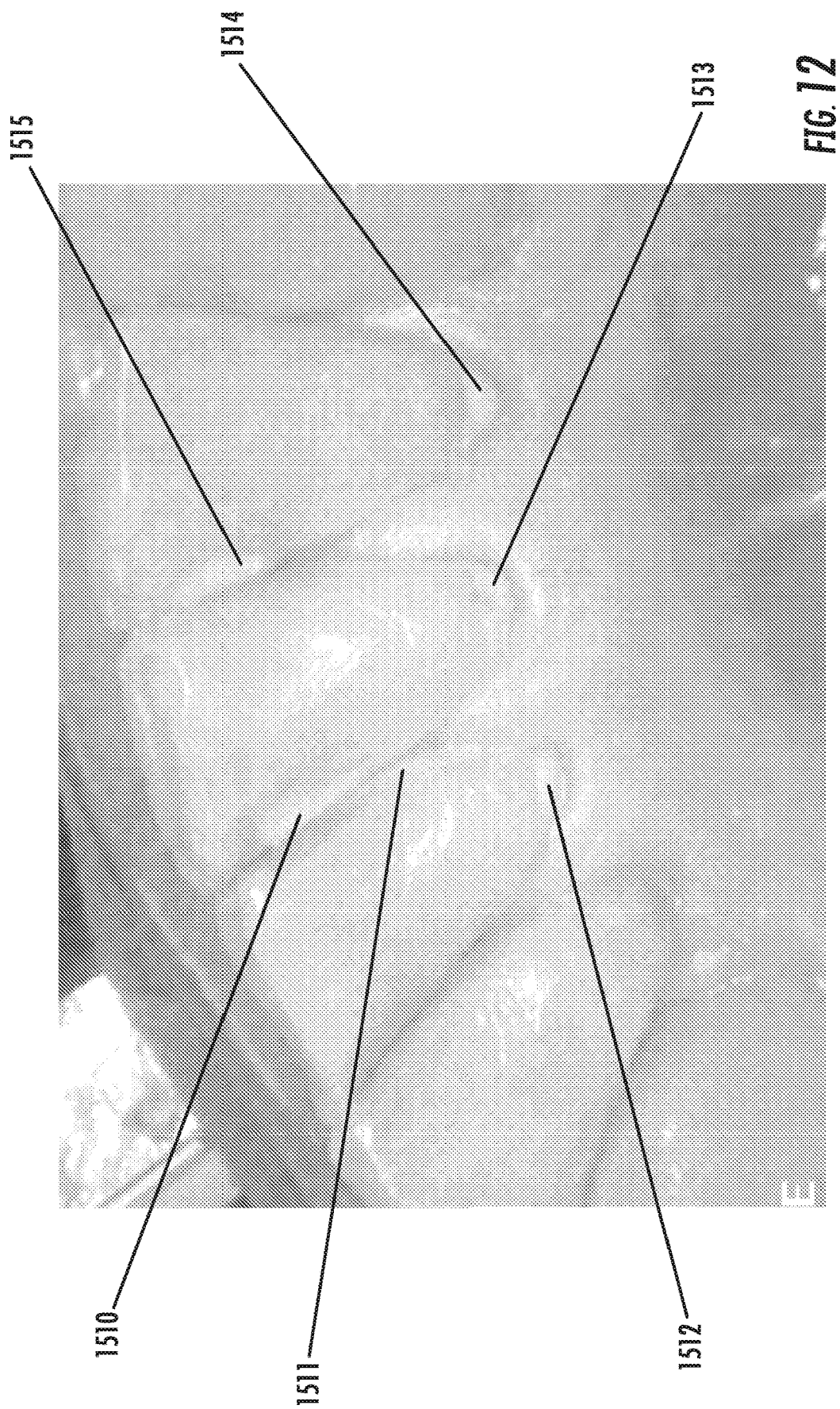
FIG. 12 illustrates tartar buildup with chlorine dioxide and no DMI.

FIG. 12 show significant tartar buildup at sites 1510, 1511, 1512, 1513, 1514, and 1515 after using CloSYS® toothpaste after flossing with Reach® waxed floss and brushing twice per day with a Philips Sonicare® toothbrush with a new compact Diamondclean® head for two minutes. FIG. 12 shows there is a significant level of tartar at the base of each tooth and between the teeth after only three months of use.

Figure 13:
FIG. 13 illustrates tartar buildup after treatment with dimethyl isosorbide mixed with common tartar reducing toothpastes, but without chlorine dioxide.

In other unsuccessful trials dimethyl isosorbide was mixed with numerous common tartar reducing toothpastes. The following picture is typical the failed result of six months of flossing with Reach® waxed floss and brushing twice per day with these various tartar reducing toothpastes with a Philips Sonicare® toothbrush for two minutes. The DMI concentration in each case was 7.1% (w). As can be seen in FIG. 13, there is a significant level of tartar formed at the lingual base of each tooth and between the teeth after six months.

Figure 15:
FIG. 15 illustrates tartar levels after treatment with an oral care formulation including DMI and chlorine dioxide after the cleaning by the dental hygienist.
Figure 14:
FIG. 14 illustrates shows tartar levels after treatment with an oral care formulation including DMI and chlorine dioxide before a cleaning by a dental hygienist.
Figure 17:
FIG. 17 illustrates tartar levels after mouthwash treatments following the treatment of FIG. 16 but with 15.1% DMI, 0.0085% chlorine dioxide, and 84.8% water (total weight 3.065 g).

However, when DMI and chlorine dioxide were used together at an effective concentration for three months (along with twice-daily flossing and brushing for two minutes), a dramatic and unexpected reduction in tartar level was observed as shown in the following photograph. FIG. 14 shows tartar levels before cleaning, and FIG. 15 shows tartar level after cleaning by the hygienist. The white spots present in FIGS. 17 and 18 are from enamel erosion from previous years of heavy tartar presence and attack of the enamel by bacteria.

Figure 16:
FIG. 16 illustrates tartar levels after mouthwash treatments with 5.49% DMI, 0.01% chlorine dioxide and 94.5% water (total weight 3.17 g).

In a separate study, 5% DMI was mixed with 0.0094% (w) chlorine dioxide in of water [94.5% (w)]. After flossing the DMI-chlorine dioxide-water mixture was transferred to the mouth of the subject and the subject brushed the teeth for 2 minutes with Philips Sonicare®. After 6 weeks of flossing and brushing twice per day with the DMI-chlorine dioxide-water mixture, the photograph of FIG. 16 was taken. FIG. 16 shows a build-up of tartar between the lower lingual teeth and some traces of tartar at the base of the teeth.

After the picture of FIG. 16 was taken the trial formulation was changed from 5% (w) to 15% DMI 0.0085% (w) chlorine dioxide in water [84.9% (w)]. This new formulation was used for 8 weeks with the same flossing and brushing regimen used in the first 6 weeks. This study resulted in a dramatic reduction in the level of tartar and tartar was removed by simple brushing without an abrasive. The picture of FIG. 17 shows the removal of most of the tartar that had been formed using 5% (w) DMI in the first six weeks then increasing the DMI concentration to 15% (w) while holding the chlorine dioxide concentration constant at approximately 0.001% (w).

It is important to note that in this trial of 5% (w) and 15% (w) DMI, no abrasive was used to remove tartar. The removal of tartar with or without abrasives with simple brushing before this time was not considered possible. Further in this example, data are presented that show that this combination of DMI and chlorine dioxide not only removes tartar above the gum line (supragingival) but also below the gum line (subgingival).

The following studies of tartar removal where the concentration of DMI has been varied between 0% and 15% in the DMI-chlorine dioxide formulation were conducted:

0% (w) DMI (0.5 to 1 ml of 0.001% (w) chlorine dioxide)—Three months of flossing and brushing with this toothpaste formulation resulted in appreciable hard tartar between the lower lingual front teeth and at the tooth gum line at the lingual base of the teeth. Lower levels of hard tartar were present throughout the tooth surfaces.

2% (w) DMI (0.5-1 ml 0.001% (w) chlorine dioxide)—Three months of flossing and brushing with this toothpaste formulation resulted in appreciable hard tartar between the lower lingual front teeth and at the tooth gum line at the lingual base of the teeth. Soft tartar was present on the top posterior buccal teeth.

6% (w) DMI (0.5-1 ml 0.001% (w) chlorine dioxide)—Three months of flossing and brushing with this toothpaste formulation resulted in low levels of soft tartar between the lower lingual front teeth and at the tooth gum line at the lingual base of the teeth. Soft tartar was present on the top posterior buccal teeth. The overall tartar levels were lower than that experienced with lower levels of DMI.

7% (w) DMI (0.5-5 ml 0.001% (w) chlorine dioxide)—Three and six months of flossing and brushing with multiple toothpaste formulations resulted in minimal soft tartar between the lower lingual front teeth and minimal soft tartar and at the tooth-gum line at the lingual base of the teeth. No or only trace tartar was present on the top posterior buccal teeth.

10% (w) DMI (0.5-2.5 ml 0.001% (w) chlorine dioxide)—Three and six month of flossing and brushing with this toothpaste formulation resulted in trace or no soft tartar between the lower lingual front teeth and trace or no soft tartar and at the tooth-gum line at the lingual base of the teeth. No tartar was present on the top posterior buccal teeth.

12-15% (w) DMI (0.5-2.5 ml 0.001% (w) chlorine dioxide)—Three and six month of flossing and brushing with this toothpaste formulation resulted in no tartar between the lower lingual front teeth and no tartar and at the tooth gum line at the lingual base of the teeth. No tartar was present on the top posterior buccal teeth. In addition to the complete removal of tartar above the gum line, users experienced the removal of subgingival tartar below the gum line at these and at the 10% (w) DMI level. Not only was tartar removed below the gum line, but people with deep gum pockets experienced significant gum reattachment to their teeth.

Tartar Removal Based on DMI Concentration

Together DMI and chlorine dioxide appear to fragment the insoluble glucan and polypeptide matrix, which holds the tartar together. Neither chlorine dioxide nor DMI alone show the ability to fragment this matrix. While not intending to be held to any specific mechanism of action, it appears that the primary role of chlorine dioxide is to break polypeptide linkages and protein polyol linkages. This ability alone, however, is insufficient to remove tartar. The water insoluble glucan matrix appears to provide much of the glue to keep the tartar intact. DMI, however, appears to enter the cracks within the glucan structure and splay out the glucan structure which promotes the entry of water to rehydrate the glucan and destabilize and fragment the biofilm and fragment the tartar structure. Thus even at very low concentrations of DMI some tartar is being removed, but the amount that is being removed is low compared to the rate of normal tartar built up. As the DMI concentration increases, the hardness of the tartar as reported by dental hygienist decreases. As a result, it is much easier to remove. At the same time as the level of DMI increases, the amount of glucans that are splayed, rehydrated, and fragmented increases as indicated by the softening of the tartar and lessening in levels of tartar present on the teeth. When the level of tartar removal is the same or greater than the level of tartar creation the dentist or hygienist will report no tartar present. For heavy tartar producers, this level of DMI appears to be between 8% (w) and 10% (w). For light tartar producers this level appears to be around 5% (w) or 8% (w) DMI. At levels above 10% (w) preexisting tartar is removed fairly rapidly. One heavy tartar producer trialed DMI at 2% (w) and found hard tartar on the lower teeth after three months but the overall level of tartar was less than that found by the same individual who used 0% (w) DMI. One test participant found that 10% (w) DMI with 1 ml of 0.001% (w) chlorine dioxide removed all tartar when used only once per day. Other test participants are reporting similar findings.

Earlier in this discussion, the tartar formation process was proposed as an equation $T_{24\ hour} = K \times P$ where the tartar amount formed over a 24 hour period is related to K, where K is a tartar formation constant and P, where P represents personal tartar variables such as saliva formation rate and the concentration of calcium and phosphate ions, pH, bacteria and saccharide sources and concentrations. Based on the tartar removal trial discussion one could postulate the following simple relationship as an equation to explain the tartar removal process:

$$T_{current} = T_{24\ hour} - T_{removed}$$

$T_{current}$ is the tartar that is present on the tooth surface
  Value=0 After a professional cleaning
  Value=0 If $T_{24\ hour}$ is less than $T_{removed}$
  Value>0 If $T_{24\ hour}$ is greater than $T_{removed}$ $T_{24\ hour}$ is the total amount of tartar produced over 24 hours by an individual. Tartar producers can be loosely grouped into four categories: Non tartar producers, light tartar producer, medium tartar producer and heavy tartar producers. Supersaturation of saliva and plaque fluids with respect to calcium phosphates is the driving force for tartar formation. Both salivary flow and plaque pH influence the rate of tartar formation. These factors are different for each individual.

$T_{removed}$ is the ability of DMI and chlorine dioxide in synergistic combination to penetrate, rehydrate and fragment tartar so that it can be washed away in the brushing process with or without abrasives. This removal efficiency is dependent on the levels of DMI and chlorine dioxide.

Chlorine Dioxide Levels

Various chlorine dioxide levels were used to study toothpaste and mouthwash formulations. Chlorine dioxide concentrations typically ranged between 0.002% (w) and 0.02% (w) with a limited trial at 0.001% (w). These concentrations were used in a number of mouthwash and toothpaste formulations. The ability to remove or reduce the formation of tartar appeared to be less dependent on the levels of chlorine dioxide than the levels of DMI. One proposed role for chlorine dioxide is the cleavage of polypeptide and peptide glycoside linkages within the tartar matrix. Even at its lowest ranges, chlorine dioxide levels seemed sufficient to cleave critical polypeptide linkages to allow the re hydration and fragmentation of the tartar matrix. Zero (0% (w)) levels of chlorine dioxide were insufficient to allow DMI alone to rehydrate and fragment the tartar matrix.

Example 6

Exemplary Veterinary Formulations
Canine/Feline tartar paste removal formulation
Weight % name
45% sorbitol
7% Glycerine
5% PEG-600
14% dimethyl isosorbide
0.1% stabilized chlorine dioxide
1% natural poultry flavoring
0.1% sodium saccharin
0.3% carboxymethyl cellulose
22.5% Hydrated Silica
5% Titanium Dioxide
Variable Disodium phosphate/Monosodium phosphate buffer
Equine tartar removal formulation
45% sorbitol
7% Glycerine
5% PEG-600
14% dimethyl isosorbide
0.1% stabilized chlorine dioxide
1% malt flavoring
0.1% sodium saccharin
0.3% carboxymethyl cellulose
22.5% Hydrated Silica
5% Titanium Dioxide
Variable Disodium phosphate/Monosodium phosphate buffer The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings. Modifications of the above-described modes for carrying out the invention that are obvious to persons of skill in the art are intended to be within the scope of the following claims.

What is claimed is:

1. An oral care formulation comprising at least one dianhydrohexitol and at least one of active chlorine dioxide or stabilized chlorine dioxide, wherein the at least one dianhydrohexitol is at a concentration of 3% (w) to 90% (w), and said oral care formulation softens dental tartar such that the dental tartar can be removed by brushing.

2. The oral care formulation of claim 1, wherein the at least one dianhydrohexitol comprises dimethyl isosorbide.

3. The oral care formulation of claim 2, wherein the dimethyl isosorbide is at a concentration of 3% (w) to 90% (w), and the at least one of active chlorine dioxide or stabilized chlorine dioxide is at a concentration of at least 0.001% (w).

4. The oral care formulation of claim 2, wherein the at least one of active chlorine dioxide or stabilized chlorine dioxide is at a concentration from 0.001% (w) to 0.08% (w).

5. The oral care formulation of claim 1, wherein the at least one dianhydrohexitol is selected from the group consisting of dimethylisosorbide, isosorbide, methyl isosorbide, isomannide, methyl isomannide, dimethyl isomannide, isoiclide, methyl isoiclide, dimethyl isoidide, isodulcide, dimethyl isodulcide.

6. The oral care formulation of claim 5, wherein the at least one of active chlorine dioxide or stabilized chlorine dioxide is at a concentration of at least 0.001% (w).

7. The oral care formulation of claim 2, wherein the dimethylisosorbide is at a concentration from 3% (w) to 40% (w); and the at least one of active chlorine dioxide or stabilized chlorine dioxide is at a concentration from 0.001% (w) to 0.08% (w).

8. The oral care formulation of claim 1 further comprising an orally acceptable carrier.

9. The oral care formulation of claim 1 further comprising an orally acceptable carrier without abrasives.

10. The oral care formulation of claim 1, wherein the oral care formulation is a dentifrice.

11. The oral care formulation of claim 1, wherein the oral care formulation is a gel.

12. The oral care formulation of claim 1, wherein the oral care formulation is a mouthwash.

13. The oral care formulation of claim 1, wherein the oral care formulation is a dental floss.

14. The oral care formulation of claim 1, wherein the oral care formulation is a chewing gum.

15. The oral care formulation of claim 1, wherein the oral care formulation is a lozenge.

16. The oral care formulation of claim 1, wherein the active chlorine dioxide is formed immediately before use of the oral care formulation by mixing a composition comprising the stabilized chlorine dioxide and pH stabilizers with a separate composition comprising a weak acid, wherein the stabilized chlorine dioxide comprises an alkaline metal chlorite.

17. The oral care formulation of claim 1, wherein the active chlorine dioxide is formed immediately before use of the oral care formulation by mixing a composition comprising the stabilized chlorine dioxide and pH stabilizers with a separate composition comprising a weak acid, wherein the stabilized chlorine dioxide comprises alkaline earth metal chlorite.

18. The oral care formulation of claim 1 comprising water.

19. The oral care formulation of claim 1, wherein the at least one dianhydrohexitol is an analog of dimethylisosorbide.

20. An oral care formulation comprising at least one dianhydrohexitol and at least one of active chloride dioxide or stabilized chlorine dioxide, wherein the at least one dianhydrohexitol is at a concentration of 2% (w) to 90% (w) and the at least one of active chloride dioxide or stabilized chlorine dioxide is at a concentration of 0.001% (w) to 0.08% (w), and said oral care formulation softens dental tartar such that the dental tartar can be removed by brushing.

21. An oral care formulation comprising at least one dianhydrohexitol or monoanhydrohexitol and at least one of active chlorine dioxide or stabilized chlorine dioxide, wherein the at least one dianhydrohexitol or monoanhydrohexitol is at a concentration of 2% (w) to 90% (w) and the at least one of active chlorine dioxide or stabilized chlorine dioxide is at a concentration of 0.001% (w) to 0.08% (w), and said oral care formulation softens dental tartar such that the dental tartar can be removed by brushing.

* * * * *